US008288608B2

(12) United States Patent
Kontsekovà et al.

(10) Patent No.: US 8,288,608 B2
(45) Date of Patent: Oct. 16, 2012

(54) TRANSGENIC ANIMAL EXPRESSING ALZHEIMER'S TAU PROTEIN

(75) Inventors: Eva Kontsekovà, Sencec (SK); Peter Filipcik, Bratislava (SK)

(73) Assignee: AXON Neuroscience SE, Bratislava (SK)

( * ) Notice: Subject to any disclaimer, the term of this patent is extended or adjusted under 35 U.S.C. 154(b) by 0 days.

(21) Appl. No.: 10/521,049

(22) PCT Filed: Jul. 9, 2003

(86) PCT No.: PCT/EP03/07390
§ 371 (c)(1),
(2), (4) Date: Nov. 1, 2005

(87) PCT Pub. No.: WO2004/007722
PCT Pub. Date: Jan. 22, 2004

(65) Prior Publication Data
US 2006/0112437 A1 May 25, 2006

(30) Foreign Application Priority Data
Jul. 12, 2002 (AT) ................................. A 1053/2002

(51) Int. Cl.
A01K 67/027 (2006.01)
A01K 67/033 (2006.01)
(52) U.S. Cl. ............................................ 800/14; 800/12
(58) Field of Classification Search .................... 800/18, 800/3, 12, 25
See application file for complete search history.

(56) References Cited

U.S. PATENT DOCUMENTS
2002/0010947 A1* 1/2002 Gurney et al. .................. 800/12

FOREIGN PATENT DOCUMENTS
WO WO 94/18560 8/1994

OTHER PUBLICATIONS

Sanders Williams et al., Transgenic animals in integrative biology: approaches and interpretations of outcome. Appl Physiol 88: 1119-1126, 2000.*
Hammer et al., Genetic engineering of mammalian embryos.J Anim Sci. Jul. 1986;63(1):269-78.*
Hammer et al.,Spontaneous inflammatory disease in transgenic rats expressing HLA-B27 and human beta 2m: an animal model of HLA-B27-associated human disorders. Cell. Nov. 30, 1990;63(5):1099-112.*
Sigmund. Viewpoint: are studies in genetically altered mice out of control?Arterioscler Thromb Vasc Biol. Jun. 2000;20(6):1425-9. Review.*
Logan et al., Potential use of genetically modified pigs as organ donors for transplantation into humans. Clin Exp Pharmacol Physiol. Dec. 1999;26(12):1020-5. Review.*
Ngo et al., Merz et al., ed. "The protein folding problem and tertiary structure prediction", Birkhauser, 1994, pp. 491-495.*
J.A. Parsons, ed. "Peptide hormones", University Park Press, 1976, pp. 1-7.*
Shuman, Producion of transgenic birds. Experentia 47, 1991, pp. 897-905.*
Zilka et al., FEBS Lett. Jun. 26, 2006;580(15):3582-8. Epub May 22, 2006Truncated tau from sporadic Alzheimer's disease suffices to drive neurofibrillary degeneration in vivo.*
Hrnkova M et al., Neurodegeneration caused by expression of human truncated tau leads to progressive neurobehavioural impairment in transgenic rats, Brain Res. Jan. 26, 2007;1130(1):206-13. Epub Dec. 13, 2006.*
Voet et al., Biochemistry John Wiley and Sons, 1990, pp. 126-128.*
Kimchi-Sarfaty C et al., A "silent" polymorphism in the MDR1 gene changes substrate specificity.Science. Jan. 26, 2007:315(5811):525-8. Epub Dec. 21, 2006.*
Moreadith RW,Gene targeting in embryonic stem cells: the new physiology and metabolism. J Mol Med. Mar. 1997;75(3):208-16.*
Keefer, Production of bioproducts through the use of transgenic animal models. Anim Reprod Sci. Jul. 2004;82-83:5-12. Review.*
Kappel, Regulating gene expression in transgenic animals. Current Biology, 3:548-553, 1992.*
Goedert et al Multiple isoforms of human microtubule-associated protein tau: sequences and localization in neurofibrillary tangles of Alzheimer's disease Neuron vol. 3, Issue 4, Oct. 1989, pp. 519-526.*
Goedert et al., Cloning and sequencing of the cDNA encoding an isoform of microtubule-associated protein tau containing four tandem repeats: differential expression of tau protein mRNAs in human brain. EMBO J. Feb. 1989;8(2):393-9.*
Novak, "Truncated tau protein as a new marker for alzheimer's disease," *Acta Virologica*, 38:173-189, 1994.
Philippe et al., "Generation of a monoclonal antibody to the carboxy-terminal domain of tau by immunization with the amino-terminal domain of the amyloid precursor protein," *J of Neuroscience Research*, 46:709-719, 1996.

(Continued)

*Primary Examiner* — Maria Leavitt
(74) *Attorney, Agent, or Firm* — Finnegan, Henderson, Farabow, Garrett & Dunner LLP

(57) ABSTRACT

The present invention provides transgenic non-human animals and non-human mammalian somatic and germ cells harbouring a human DNA sequence encoding Alzheimer's Disease (AD) derived tau protein, capable of inducing AD pathology in transgenic animals. Alzheimer's tau protein is expressed on specific genetic backgrounds allowing also simulation of different human diseases including hypertension, diabetes, hyper-cholesterolemia, which are associated with neurodegeneration and are considerable risk factors for AD development. Transgenic animals and cells of the present invention exhibit neurofibrillary pathology and may serve as in vivo and also in vitro assay systems for screening and developing therapeutic and preventive substances and also diagnostic markers and probes for tauopathies and AD. Furthermore these transgenic animals and cell lines derived thereof provide an in vivo and in vitro assay system for neurodegenerative disorders preferably tauopathies and AD which are the result of combinations with other disease as hypertension and others representing risk factors associated with the process of neurodegeneration.

6 Claims, 10 Drawing Sheets

OTHER PUBLICATIONS

Ugolini et al., "Co-localization of truncated tau and dna fragmentation in alzheimer's disease neurones," *NeuroReport*, 8:3709-3712, 1997.

Zemlan et al., "Quantification of axonal damage in traumatic brain injury: affinity purification an dcharacterization of cerebrospinal fluid tau proteins," *J of Neurochemicstry*, 72:741-750, 1999.

Abraha et al., "C-terminal inhibition of tau assembly in vitro and in alzheimer's disease," *J of Cell Science*, 113:3737-3745, 2000.

Brandt et al., "Functional organization of microtubule-associated protein tau," *The J of Biological Chemistry*, 268:3414-3419, 1993.

Esposito et al., "The solution structure of the c-terminal segment of tau protein," *J of Peptide Science*, 6:550-559, 2000.

Fasulo et al., "Tau truncation in alzheimer's disease: expression of a fragment encompassing phf core tau induces apoptosis in cos cells," *Alzheimer's Reports*, 1:25-32, 1998.

Fasulo et al., "The neuronal microtubule-associated protein tau is a substrate for caspase-3 and an effector of apoptosis," *J of Neurochemistry*, 75:624-633, 2000.

Jicha et al., "Sequence requirements for formation of conformational variants of tau similar to those found in alzheimer's disease," *J of Neuroscience Research*, 55:713-723, 1999.

Kontsekova et al., "Quick purification of recombinant human truncated tau proteins for immunoanalysis," *J of Immunological Methods*, 185:245-248, 1995.

Novak et al., "Molecular characterization of the minimal protease resistant tau unit of the alzheimer's disease paried helical filament," *The EMBO Journal*, 12:365-370, 1993.

Novak et al., "Truncation of tau precedes fragmentation of dna in alzheimer's disease," *Chm. Papers*, 52:429-430, 1998.

Braak et al., "Staging of Alzheimer disesase-associated neurofibrillary pathology using paraffin sections and immunocytochemistry," *Acta Neuropathol*, 112:389-404, 2006.

Cente et al., "Expression of a truncated tau protein induces oxidative stress in a rodent model of tauopathy," *European Journal of Neuroscience*, 24:1085-1090, 2006.

Fitzsimons et al., "Promoters and regulatory elements that improve adeno-associated virus transgene expression in the brain," *Methods*, 28:227-236, 2002.

Götz et al., "Tau and transgenic animal models," *Brain Research Reviews*, 35:266-286, 2001.

Härtig et al., "Hibernation model of tau phosphorylation in hamsters: selective vulnerability of cholinergic basal forebrain neurons—implications for Alzheimer's disease," *European Journal of Neuroscience*, 25:69-80, 2007.

Huang et al., "Neurofibrillary lesions in experimental aluminum-induced encephalopathy and Alzheimer's disease share immunoreactivity for amyloid precursor protein, A β, $\alpha_1$-antichymotrypsin and ubiquitin-protein conjugates," *Brain Research*, 771:213-220, 1997.

Lewis et al., "Neurofibrillary tangles, amyotrophy and progressive motor disturbance in mice expressing mutant (P301L) tau protein," *Nature Genetics*, 25:402-405, 2000.

Vercauteren et al., "Early dysregulation of hippocampal proteins in transgenic rats with Alzheimer's disease-linked mutations in amyloid precursor protein and presenilin 1," *Molecular Brain Research*, 132:241-259, 2004.

Wang et al., "Diverse stabilities of expression in the rat brain from different cellular promoters in a helper virus-free herpes simplex virus type 1 vector system," *Human Gene Therapy*, 10:1763-1771, 1999.

\* cited by examiner numbering of the *tau 43* nucleotides represented by SEQ ID NO: 1-9 is according to the shortest R4 isoform (*tau 43*, nucleotides 1 through 1149, represented in the first row of the above figure);

numbering of the *tau 44* nucleotides represented by SEQ ID NO: 10-14 is according to the shortest R3 isoform (*tau 44*, nucleotides 1 through 1056, represented in the sixth row from the bottom in the above figure)

FIGURE 1

| Human brain tissue, autopsy from AD patient | Transgenic rat brain tissue TG line Nr. 318 |
|---|---|
|  A |  B |
|  C |  D |
|  E |  F |

SEQUENCE LISTING

<160> NUMBER OF SEQ ID NOS: 19

<210> SEQ ID NO 1
<211> LENGTH: 969
<212> TYPE: DNA
<213> ORGANISM: human

<400> SEQUENCE: 1

```
atgcaccaag accaagaggg tgacacggac gctggcctga aagctgaaga agcaggcatt      60
ggagacaccc ccagcctgga agacgaagct gctggtcacg tgacccaagc tcgcatggtc     120
agtaaaagca aagacgggac tggaagcgat gacaaaaaag ccaaggggc tgatggtaaa     180 acgaagatcg ccacaccgcg gggagcagcc cctccaggcc agaagggcca ggccaacgcc     240
accaggattc cagcaaaaac cccgcccgct ccaaagacac cacccagctc tggtgaacct     300
ccaaaatcag gggatcgcag cggctacagc agccccggct cccaggcac tcccggcagc     360 cgctcccgca ccccgtccct tccaaccca cccacccggg agcccaagaa ggtggcagtg     420
gtccgtactc cacccaagtc gccgtcttcc gccaagagcc gctgcagac agccccgtg     480 cccatgccag acctgaagaa tgtcaagtcc aagatcggct ccactgagaa cctgaagcac     540
cagccgggag gcgggaaggt gcagataatt aataagaagc tggatcttag caacgtccag     600
tccaagtgtg gctcaaagga taatatcaaa cacgtccgg gaggcggcag tgtgcaaata     660
gtctacaaac cagttgacct gagcaaggtg acctccaagt gtggctcatt aggcaacatc     720
```

```
catcataaac caggaggtgg ccaggtggaa gtaaaatctg agaagcttga cttcaaggac    780
agagtccagt cgaagattgg gtccctggac aatatcaccc acgtccctgg cggaggaaat    840
aaaaagattg aaacccacaa gctgaccttc cgcgagaacg ccaaagccaa gacagaccac    900
ggggcggaga tcgtgtacaa gtcgccagtg gtgtctgggg acacgtctcc acggcatctc    960
agcaatgtc                                                            969
```

<210> SEQ ID NO 2
<211> LENGTH: 795
<212> TYPE: DNA
<213> ORGANISM: human

<400> SEQUENCE: 2

```
atggtcagta aaagcaaaga cgggactgga agcgatgaca aaaaagccaa gggggctgat     60
ggtaaaacga agatcgccac accgcgggga gcagcccctc caggccagaa gggccaggcc    120
aacgccacca ggattccagc aaaaaccccg cccgctccaa agacaccacc cagctctggt    180
gaacctccaa aatcagggga tcgcagcggc tacagcagcc ccggctcccc aggcactccc    240
ggcagccgct cccgcacccc gtcccttcca accccaccca cccgggagcc caagaaggtg    300
gcagtggtcc gtactccacc caagtcgccg tcttccgcca gagccgcct gcagacagcc    360 cccgtgccca tgccagacct gaagaatgtc aagtccaaga tcggctccac tgagaacctg    420
aagcaccagc cgggaggcgg gaaggtgcag ataattaata agaagctgga tcttagcaac    480
gtccagtcca agtgtggctc aaaggataat atcaaacacg tcccgggagg cggcagtgtg    540
caaatagtct acaaaccagt tgacctgagc aaggtgacct ccaagtgtgg ctcattaggc    600
aacatccatc ataaaccagg aggtggccag gtggaagtaa aatctgagaa gcttgacttc    660
aaggacagag tccagtcgaa gattgggtcc ctggacaata tcacccacgt ccctggcgga    720
ggaaataaaa agattgaaac ccacaagctg accttccgcg agaacgccaa agccaagaca    780
gaccacgggg cggag                                                     795
```

<210> SEQ ID NO 3
<211> LENGTH: 723
<212> TYPE: DNA
<213> ORGANISM: human

<400> SEQUENCE: 3

```
atcgccacac cgcggggagc agcccctcca ggccagaagg ccaggccaa cgccaccagg      60 attccagcaa aaaccccgcc cgctccaaag acaccaccca gctctggtga acctccaaaa    120 tcagggatc gcagcggcta cagcagcccc ggctccccag cactccggg cagccgctcc     180 cgcacccgt cccttccaac cccacccacc cgggagccca gaaggtggc agtggtccgt      240 actccaccca gtcgccgtc ttccgccaag agccgcctgc agacagcccc cgtgcccatg    300
ccagacctga agaatgtcaa gtccaagatc ggctccactg agaacctgaa gcaccagccg    360
ggaggcggga aggtgcagat aattaataag aagctggatc ttagcaacgt ccagtccaag    420
tgtggctcaa aggataatat caaacacgtc ccggggaggcg gcagtgtgca aatagtctac    480
aaaccagttg acctgagcaa ggtgacctcc aagtgtggct cattaggcaa catccatcat    540
aaaccaggag gtggccaggt ggaagtaaaa tctgagaagc ttgacttcaa ggacagagtc    600
cagtcgaaga ttgggtccct ggacaatatc acccacgtc ctggcggagg aaataaaaag    660
attgaaaccc acaagctgac cttccgcgag aacgccaaag ccaagacaga ccacggggcg    720
gag                                                                  723
```

<210> SEQ ID NO 4
<211> LENGTH: 885
<212> TYPE: DNA
<213> ORGANISM: human

<400> SEQUENCE: 4

```
atggtcagta aaagcaaaga cgggactgga agcgatgaca aaaaagccaa gggggctgat        60
ggtaaaacga agatcgccac accgcgggga gcagcccctc caggccagaa gggccaggcc       120
aacgccacca ggattccagc aaaaaccccg cccgctccaa agacaccacc cagctctggt       180
gaacctccaa atcaggggat cgcagcggc tacagcagcc ccggctcccc aggcactccc        240
ggcagccgct cccgcacccc gtcccttcca acccacccca cccgggagcc caagaaggtg       300
gcagtggtcc gtactccacc caagtcgccg tcttccgcca gagccgcct gcagacagcc        360
cccgtgccca tgccagacct gaagaatgtc aagtccaaga tcggctccac tgagaacctg       420
aagcaccagc cggaggcgg gaaggtgcag ataattaata agaagctgga tcttagcaac        480
gtccagtcca agtgtggctc aaaggataat atcaaacacg tcccggggag cggcagtgtg       540
caaatagtct acaaaccagt tgacctgagc aaggtgacct ccaagtgtgg ctcattaggc       600
aacatccatc ataaaccagg aggtggccag gtggaagtaa aatctgagaa gcttgacttc       660
aaggacagag tccagtcgaa gattgggtcc ctggacaata tcacccacgt ccctggcgga       720
ggaaataaaa agattgaaac ccacaagctg accttccgcg agaacgccaa agccaagaca       780
gaccacgggg cggagatcgt gtacaagtcg ccagtggtgt ctggggacac gtctccacgg       840
catctcagca atgtctcctc caccggcagc atcgacatgg tagac                      885
```

<210> SEQ ID NO 5
<211> LENGTH: 813
<212> TYPE: DNA
<213> ORGANISM: human

<400> SEQUENCE: 5

```
atcgccacac cgcggggagc agcccctcca ggccagaagg ccaggccaa cgccaccagg         60
attccagcaa aaaccccgcc cgctccaaag acaccaccca gctctggtga acctccaaaa       120
tcaggggatc gcagcggcta cagcagcccc ggctccccag gcactcccgg cagccgctcc       180
cgcaccccgt cccttccaac cccacccacc cgggagccca agaaggtggc agtggtccgt       240
actccacca gtcgccgtc ttccgccaag agccgcctgc agacagcccc cgtgcccatg         300
ccagacctga agaatgtcaa gtccaagatc ggctccactg agaacctgaa gcaccagccg       360
gaggcgggaa ggtgcagat aattaataag aagctggatc ttagcaacgt ccagtccaag        420
tgtggctcaa aggataatat caaacacgtc ccggaggcg gcagtgtgca aatagtctac        480
aaaccagttg acctgagcaa ggtgacctcc aagtgtggct cattaggcaa catccatcat       540
aaaccaggag gtggccaggt ggaagtaaaa tctgagaagc ttgacttcaa ggacagagtc       600
cagtcgaaga ttgggtccct ggacaatatc acccacgtcc ctggcggagg aaataaaaag       660
attgaaaccc acaagctgac cttccgcgag aacgccaaag ccaagacaga ccacggggcg       720
gagatcgtgt acaagtcgcc agtggtgtct ggggacacgt ctccacggca tctcagcaat       780
gtctcctcca ccggcagcat cgacatggta gac                                    813
```

<210> SEQ ID NO 6
<211> LENGTH: 285
<212> TYPE: DNA
<213> ORGANISM: human

<400> SEQUENCE: 6

```
atcaaacacg tcccgggagg cggcagtgtg caaatagtct acaaaccagt tgacctgagc    60
aaggtgacct ccaagtgtgg ctcattaggc aacatccatc ataaaccagg aggtggccag   120
gtggaagtaa aatctgagaa gcttgacttc aaggacagag tccagtcgaa gattgggtcc   180
ctggacaata tcacccacgt ccctggcgga ggaaataaaa agattgaaac ccacaagctg   240
accttccgcg agaacgccaa agccaagaca gaccacgggg cggag                   285
```

<210> SEQ ID NO 7
<211> LENGTH: 291
<212> TYPE: DNA
<213> ORGANISM: human

<400> SEQUENCE: 7

```
gataatatca aacacgtccc gggaggcggc agtgtgcaaa tagtctacaa accagttgac    60
ctgagcaagg tgacctccaa gtgtggctca ttaggcaaca tccatcataa accaggaggt   120
ggccaggtgg aagtaaaatc tgagaagctt gacttcaagg acagagtcca gtcgaagatt   180
gggtccctgg acaatatcac ccacgtccct ggcggaggaa ataaaaagat tgaaacccac   240
aagctgacct tccgcgagaa cgccaaagcc aagacagacc acggggcgga g            291
```

<210> SEQ ID NO 8
<211> LENGTH: 240
<212> TYPE: DNA
<213> ORGANISM: human

<400> SEQUENCE: 8

```
atcaaacacg tcccgggagg cggcagtgtg caaatagtct acaaaccagt tgacctgagc    60
aaggtgacct ccaagtgtgg ctcattaggc aacatccatc ataaaccagg aggtggccag   120
gtggaagtaa aatctgagaa gcttgacttc aaggacagag tccagtcgaa gattgggtcc   180
ctggacaata tcacccacgt ccctggcgga ggaaataaaa agattgaaac ccacaagctg   240
```

<210> SEQ ID NO 9
<211> LENGTH: 189
<212> TYPE: DNA
<213> ORGANISM: human

<400> SEQUENCE: 9

```
gtgcaaatag tctacaaacc agttgacctg agcaaggtga cctccaagtg tggctcatta    60
ggcaacatcc atcataaacc aggaggtggc caggtggaag taaaatctga agagcttgac   120
ttcaaggaca gagtccagtc gaagattggg tccctggaca atatcaccca cgtccctggc   180
ggaggaaat                                                           189
```

<210> SEQ ID NO 10
<211> LENGTH: 876
<212> TYPE: DNA
<213> ORGANISM: human

<400> SEQUENCE: 10

```
atgcaccaag accaagaggg tgacacggac gctggcctga agctgaaga agcaggcatt     60
ggagacaccc ccagcctgga agacgaagct gctggtcacg tgacccaagc tcgcatggtc   120
agtaaaagca agacgggac tggaagcgat gacaaaaaag ccaggggggc tgatggtaaa   180
acgaagatcg ccacaccgcg gggagcagcc cctccaggcc agaagggcca ggccaacgcc   240
accaggattc agcaaaaaac cccgcccgct ccaaagacac cacccagctc tggtgaacct   300
```

```
ccaaaatcag gggatcgcag cggctacagc agccccggct ccccaggcac tcccggcagc      360
cgctcccgca cccgtccct tccaacccca cccacccggg agcccaagaa ggtggcagtg      420
gtccgtactc cacccaagtc gccgtcttcc gccaagagcc gcctgcagac agcccccgtg      480
cccatgccag acctgaagaa tgtcaagtcc aagatcggct ccactgagaa cctgaagcac      540
cagccgggag cgggaaggt gcaaatagtc tacaaaccag ttgacctgag caaggtgacc      600
tccaagtgtg gctcattagg caacatccat cataaaccag gaggtggcca ggtggaagta      660
aaatctgaga agcttgactt caaggacaga gtccagtcga agattgggtc cctggacaat      720
atcacccacg tccctggcgg aggaaataaa aagattgaaa cccacaagct gaccttccgc      780
gagaacgcca agccaagac agaccacggg gcggagatcg tgtacaagtc gccagtggtg      840
tctggggaca cgtctccacg gcatctcagc aatgtc                                876

<210> SEQ ID NO 11
<211> LENGTH: 702
<212> TYPE: DNA
<213> ORGANISM: human

<400> SEQUENCE: 11
atggtcagta aaagcaaaga cgggactgga agcgatgaca aaaagccaa gggggctgat       60 ggtaaaacga agatcgccac accgcgggga gcagcccctc caggccagaa gggccaggcc      120
aacgccacca ggattccagc aaaaaccccg cccgctccaa agacaccacc cagctctggt      180
gaacctccaa atcagggga tcgcagcggc tacagcagcc ccggctcccc aggcactccc      240
ggcagccgct cccgcacccc gtcccttcca accccaccca cccgggagcc caagaaggtg      300
gcagtggtcc gtactccacc caagtcgccg tcttccgcca agagccgcct gcagacagcc      360
cccgtgccca tgccagacct gaagaatgtc aagtccaaga tcggctccac tgagaacctg      420
aagcaccagc cgggaggcgg gaaggtgcaa atagtctaca accagttga cctgagcaag      480 gtgacctcca gtgtggctc attaggcaac atccatcata accaggagg tggccaggtg      540 gaagtaaaat ctgagaagct tgacttcaag gacagagtcc agtcgaagat tgggtccctg      600
gacaatatca cccacgtccc tggcggagga aataaaaaga ttgaaaccca caagctgacc      660
ttccgcgaga acgccaaagc caagacagac cacggggcgg ag                        702

<210> SEQ ID NO 12
<211> LENGTH: 630
<212> TYPE: DNA
<213> ORGANISM: human

<400> SEQUENCE: 12
atcgccacac cgcggggagc agcccctcca ggccagaagg gccaggccaa cgccaccagg       60
attccagcaa aaaccccgcc cgctccaaag acaccaccca gctctggtga acctccaaaa      120 tcagggggatc gcagcggcta cagcagcccc ggctccccag cactcccgg cagccgctcc      180 cgcaccccgt cccttccaac ccacccacc cgggagccca agaaggtggc agtggtccgt      240
actccaccca agtcgccgtc ttccgccaag agccgcctgc agacagcccc cgtgcccatg      300
ccagacctga gaatgtcaa gtccaagatc ggctccactg agaacctgaa gcaccagccg      360
ggaggcggga aggtgcaaat agtctacaaa ccagttgacc tgagcaaggt gacctccaag      420
tgtggctcat taggcaacat ccatcataaa ccaggaggtg gccaggtgga agtaaaatct      480
gagaagcttg acttcaagga cagagtccag tcgaagattg gtccctga caatatcacc      540 cacgtccctg gcggaggaaa taaaaagatt gaaacccaca agctgacctt ccgcgagaac      600
```

```
gccaaagcca agacagacca cggggcggag                                    630

<210> SEQ ID NO 13
<211> LENGTH: 792
<212> TYPE: DNA
<213> ORGANISM: human

<400> SEQUENCE: 13
atggtcagta aaagcaaaga cgggactgga agcgatgaca aaaaagccaa ggggggctgat    60
ggtaaaacga agatcgccac accgcgggga gcagcccctc caggccagaa gggccaggcc   120
aacgccacca ggattccagc aaaaaccccg cccgctccaa agacaccacc cagctctggt   180
gaacctccaa aatcagggga tcgcagcggc tacagcagcc ccggctcccc aggcactccc   240
ggcagccgct cccgcacccc gtcccttcca accccaccca cccgggagcc caagaaggtg   300
gcagtggtcc gtactccacc caagtcgccg tcttccgcca agagccgcct gcagacagcc   360
cccgtgccca tgccagacct gaagaatgtc aagtccaaga tcggctccac tgagaacctg   420
aagcaccagc cggaggcgg gaaggtgcaa atagtctaca accagttgac cctgagcaag   480
gtgacctcca agtgtggctc attaggcaac atccatcata aaccaggagg tggccaggtg   540
gaagtaaaat ctgagaagct tgacttcaag gacagagtcc agtcgaagat tgggtccctg   600
gacaatatca cccacgtccc tggcggagga aataaaaaga ttgaaaccca aagctgacc   660
ttccgcgaga acgccaaagc caagacagac cacggggcgg agatcgtgta caagtcgcca   720
gtggtgtctg ggacacgtc tccacggcat ctcagcaatg tctcctccac cggcagcatc   780
gacatggtag ac                                                        792

<210> SEQ ID NO 14
<211> LENGTH: 720
<212> TYPE: DNA
<213> ORGANISM: human

<400> SEQUENCE: 14
atcgccacac cgcggggagc agcccctcca ggccagaagg gccaggccaa cgccaccagg    60
attccagcaa aaaccccgcc cgctccaaag acaccaccca gctctggtga acctccaaaa   120
tcaggggatc gcagcggcta cagcagcccc ggctccccag cactcccgg cagccgctcc   180
cgcaccccgt cccttccaac cccacccacc cgggagccca gaaggtggc agtggtccgt   240
actccaccca agtcgccgtc ttccgccaag agccgcctgc agacagcccc cgtgcccatg   300
ccagacctga agaatgtcaa gtccaagatc ggctccactg agaacctgaa gcaccagccg   360
gaggcgggga aggtgcaaat agtctacaaa ccagttgacc tgagcaaggt gacctccaag   420
tgtggctcat taggcaacat ccatcataaa ccaggaggtg gccaggtgga agtaaaatct   480
gagaagcttg acttcaagga cagagtccag tcgaagattg gtccctgga caatatcacc   540
cacgtccctg gcggaggaaa taaaagatt gaaacccaca agctgacctt ccgcgagaac   600
gccaaagcca agacagacca cggggcggag atcgtgtaca agtcgccagt ggtgtctggg   660
gacacgtctc cacggcatct cagcaatgtc tcctccaccg gcagcatcga catggtagac   720

<210> SEQ ID NO 15
<211> LENGTH: 2946
<212> TYPE: DNA
<213> ORGANISM: human

<400> SEQUENCE: 15
aatgtcccga attccagcc tcaccacccc ttctcagtaa tgaccctggt tggttgcagg    60
```

```
aggtacctac tccatactga gggtgaaatt aagggaaggc aaagtccagg cacaagagtg    120
ggaccccagc ctctcactct cagttccact catccaactg ggaccctcac cacgaatctc    180
atgatctgat tcggttccct gtctcctcct cccgtcacag atgtgagcca gggcactgct    240
cagctgtgac cctaggtgtt tctgccttgt tgacatggag agagcccttt cccctgagaa    300
ggcctggccc cttcctgtgc tgagcccaca gcagcaggct gggtgtcttg gttgtcagtg    360
gtggcaccag gatggaaggg caaggcaccc agggcaggcc cacagtcccg ctgtccccca    420
cttgcaccct agcttgtagc tgccaacctc ccagacagcc cagcccgctg ctcagctcca    480
catgcatagt atcagccctc cacacccgac aaagggaaac accccccttg gaaatggtt     540 cttttccccc agtcccagct ggaagccatg ctgtctgttc tgctggagca gctgaacata    600
tacatagatg ttgccctgcc ctccccatct gcacctgtt gagttgtagt tggatttgtc     660
tgtttatgct tggattcacc agagtgacta tgatagtgaa agaaaaaaa aaaaaaaaa      720 aggacgcatg tatcttgaaa tgcttgtaaa gaggtttcta acccaccctc acgaggtgtc    780
tctcaccccc acactgggac tcgtgtggcc tgtgtggtgc caccctgctg ggcctccca    840 agttttgaaa ggctttcctc agcacctggg acccaacaga gaccagcttc tagcagctaa    900
ggaggccgtt cagctgtgac gaaggcctga agcacaggat taggactgaa gcgatgatgt    960 cccccttccct acttccccctt ggggctccct gtgtcagggc acagactagg tcttgtggct   1020
ggtctggctt gcggcgcgag gatggttctc tctggtcata gcccgaagtc tcatggcagt   1080
cccaaaggag gcttacaact cctgcatcac aagaaaaagg aagccactgc cagctggggg   1140
gatctgcagc tcccagaagc tccgtgagcc tcagccaccc ctcagactgg gttcctctcc   1200
aagctcgccc tctggagggg cagcgcagcc tcccaccaag ggccctgcga ccacagcagg   1260
gattgggatg aattgcctgt cctggatctg ctctagaggc ccaagctgcc tgcctgagga   1320
aggatgactt gacaagtcag gagacactgt tcccaaagcc ttgaccagag cacctcagcc   1380
cgctgacctt gcacaaactc catctgctgc catgagaaaa gggaagccgc ctttgcaaaa   1440
cattgctgcc taaagaaact cagcagcctc aggcccaatt ctgccacttc tggtttgggt   1500
acagttaaag gcaaccctga gggacttggc agtagaaatc cagggcctcc cctggggctg   1560
gcagcttcgt gtgcagctag agctttacct gaaaggaagt ctctgggccc agaactctcc   1620
accaagagcc tccctgccgt tcgctgagtc ccagcaattc tcctaagttg aagggatctg   1680
agaaggagaa ggaaatgtgg ggtagatttg gtggtggtta gagatatgcc ccctcatta    1740 ctgccaacag tttcggctgc atttcttcac gcacctcggt tcctcttcct gaagttcttg   1800
tgccctgctc ttcagcacca tgggccttct tatacggaag gctctgggat ctccccttg    1860 tggggcaggc tcttggggcc agcctaagat catggtttag ggtgatcagt gctggcagat   1920
aaattgaaaa ggcacgctgg cttgtgatct taaatgagga caatcccccc agggctgggc   1980
actcctcccc tcccctcact tctcccacct gcagagccag tgtccttggg tgggctagat   2040
aggatatact gtatgccggc tccttcaagc tgctgactca ctttatcaat agttccattt   2100
aaattgactt cagtggtgag actgtatcct gtttgctatt gcttgttgtg ctatgggggg   2160 agggggagg aatgtgtaag atagttaaca tgggcaaagg gagatcttgg ggtgcagcac    2220
ttaaactgcc tcgtaaccct tttcatgatt tcaaccacat ttgctagagg gagggagcag   2280
ccacggagtt agaggccctt ggggtttctc ttttccactg acaggctttc ccaggcagct   2340
ggctagttca ttccctcccc agccaggtgc aggcgtagga atatgacat ctggttgctt    2400 tggcctgctg ccctctttca ggggtcctaa gcccacaatc atgcctccct aagaccttgg   2460
```

```
catccttccc tctaagccgt tggcacctct gtgccacctc tcacactggc tccagacaca      2520
cagcctgtgc ttttggagct gagatcactc gcttcaccct cctcatcttt gttctccaag      2580
taaagccacg aggtcgggc gagggcagag gtgatcacct gcgtgtccca tctacagacc       2640
tgcagcttca taaaacttct gatttctctt cagctttgaa aagggttacc ctgggcactg      2700
gcctagagcc tcacctccta atagacttag ccccatgagt ttgccatgtt gagcaggact      2760
atttctggca cttgcaagtc ccatgatttc ttcggtaatt ctgagggtgg ggggagggac      2820
atgaaatcat cttagcttag ctttctgtct gtgaatgtct atatagtgta ttgtgtgttt      2880
taacaaatga tttacactga ctgttgctgt aaaagtgaat ttggaaataa agttattact      2940
ctgatt                                                                 2946
```

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
gtggatctca agccctcaag                                                      20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
gatcccctga ttttggaggt                                                      20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18
aaggtgacct ccaagtgtgg                                                      20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
ggtatgcatg gagggagaag                                                      20
```

TRANSGENIC ANIMAL EXPRESSING ALZHEIMER'S TAU PROTEIN

This application is a national phase application under 35 U.S.C. §371 of International Application No. PCT/EP2003/007390 filed 9 Jul. 2003, which claims priority to Austrian Application No. A 1053/2002 filed 12 Jun. 2002, the contents of which applications are incorporated herein by reference in their entirety.

Neurodegenerative diseases represent a heterogeneous group of genetic and acquired neurological disorders that result in severe and progressive cognitive and motor impairment with on-set during mid- to late-life (1). The most common cause of dementia is Alzheimer's disease. In less than 5% of the cases Alzheimer's disease genetic factors are involved, the rest of cases are sporadic.

Tau protein is the protein expressed in central nervous system and plays a critical role in the neuronal architecture by stabilizing intracellular microtubule network. Impairment of the physiological role of the tau protein either by truncation, hyperphosphorylation or by disturbing the balance between the six naturally occurring tau isoforms leads to the formation of neurofibrillary tangles (NFT), dystrophic neurites and neuropil threads. These structures represent ultrastructural hallmarks of Alzheimer's disease. The major protein subunit of these structures is microtubule associated protein tau (2, 3). The amount of NFT found in autopsies of AD patients correlates with clinical symptoms including intellectual decline. Therefore tau protein plays a critical role in AD pathology. The recent discovery of cosegregation of specific mutations in the tau gene with the disease frontotemporal dementia with Parkinsonism linked to chromosome 17 (FTDP-17) has confirmed that certain abnormalities in the tau protein can be a primary cause of neurodegeneration and dementia in affected individuals (4, 5). However there is no experimental model that would directly address the details on the role of tau protein in pathogenesis of AD.

Recent transgenic models of AD are based on expression of proteins associated with FAD (APP, PS1, ApoE etc.) either mutated or not. They include single and multigenic humanized animals.

However none of the models recapitulates both hallmarks of AD, they usually do not show neurofibrillary pathology and none of them includes the possibility of investigation of function of environmental risk factors, which play a major role in the development of AD.

Currently available animal models showing some neurofibrillary changes are based solely on transgenic expression of mutated tau derived from frontotemporal dementia linked to chromosome 17 (FTDP17). Typical example of this group is JNPL3 transgenic mouse (6). Another evidence on the role of mutated tau have been published recently by Goedert and Spillantini (7).

In another transgenic animal model an overexpression of four repeat tau protein was investigated. Prominent axonopathy in the brain and spinal cord was reported and it was shown that an overexpression of four repeat tau protein isoform is sufficient to alter physiology of neurons. In the model, axonal dilations with accumulation of neurofilaments were documented in the neurons of central nervous system however without formation, however of intraneuronal neurofibrillary tangles (8).

The transgenic mouse was also produced in order to examine the normal cellular function of tau and its role in pathogenesis. The transgenic mouse overexpress a genomic tau transgene and also tau cDNA transgene. The comparison of two models shows that the distribution of tau is similar in both transgenic lines. Tau-immunoreactive axonal swellings were found in the spinal cords of the cDNA mice, which correlated with a hind-limb abnormality, whereas neuropathology was not observed in the genomic mice (9).

Despite of the advantage of rat as an experimental model in neurobiology in comparison to mice, it is surprising that no tau transgenic model for neurofibrillary pathology was produced. In general it is considerable lower amount of transgenic rat models of neurodegeneration produced till now. None of them recapitulates tau pathology, which is typical for AD.

Czech C, et al. (12) described a transgenic rat model which comprises of mutations in the gene coded for presenilin 1 (SP1). PS1 is considered as a cause for the majority of cases of early onset familial Alzheimer's disease, however the published model did not show sufficient signs of AD associated pathology. Echeverria V and Cuello A C. (13) comment on the role of intra-cellular accumulation of beta amyloid and the possible neuropathological role of intracellular amyloid-beta accumulation in Alzheimer's disease. Their present recent observations from a rat transgenic model with a phenotype of intracellular accumulation of A-beta fragments in neurons of the hippocampus and cortex, however without plaque and NFT formation. Therefore for rats, which is the second most often used animal in transgenic studies applies the same as for mice: there is no transgenic rat described in scientific literature that would express truncated tau protein and showed NFT formation.

Till now there is no experimental model available for investigation of etiology of AD in a connection with hypertension or other risk factors like diabetes and dislipidemia, which are associated with AD. Genetic background of experimental transgenic animals plays a role in the development of appropriate transgenic model It is well known that AD is associated with certain environmental risk factors. It was shown in epidemiological studies, that risk factors for vascular disease and stroke are associated with cognitive impairment and Alzheimer's disease; moreover the presence of cerebrovascular disease intensifies the presence and severity of the clinical symptoms of Alzheimer's disease (14). Another link between hypertension and dementia of AD type is indicated in a Rotterdam Study (15).

Therefore it is important to develop an experimental model for AD, which would mimic the main pathological features of the disease and simultaneously allows an expression of environmental factors associated with AD etiology.

It is therefore an object of present invention to provide an experimental model, which reflects the hallmarks of AD as close as possible and also the assay system for substances for treatment, prevention and diagnosis of AD.

The present invention relates to a transgenic non-human animal expressing cDNA encoded Alzheimer's tau protein in the brain of the transgenic animals. These animals exhibit NF pathological activity in brains. The invention further relates to a transgenic animal, which can be used as a screening assay system in the process of identifying substances, which improve learning and memory, inhibit neurodegeneration and decrease the rate of neurofibrillary tangles (NFT) formation and their elimination from the brain. The animals can be used for identifying substances for prevention, treatment and diagnosis of neurodegenerative diseases, preferably tauopathies and AD. The transgenic animals can also be used for investigating the influence of AD associated risk factors, on the development of AD. Another use of animals lies in the process of drug target identification.

The present invention describes the engineering of transgenic animals producing AD changes induced by specific transgene, resembling Alzheimer's disease in these animals. This provides an investigative tool to the discovery and development of drugs and diagnosis and to further study the role of normal and diseased tau proteins in vivo.

The present invention relies on an induction of NF pathological activity in brain of animals solely by expressing of Alzheimer's tau protein in the brains of transgenic animals. Hallmarks of AD are induced in animals, which are prone to induction of risk factors associated with etiology of AD, which is another advantage of the present invention.

All technical and scientific terms used in the description of preferred embodiments have—unless specified otherwise—the same meaning as commonly understood in the field of art to which this invention belongs. The preferred methods, the laboratory procedures in cell culture, molecular genetics, biochemistry, and nucleic acid chemistry and materials are described in the invention, but any methods and materials similar or equivalent can be used in testing of the present invention. For procedures like recombinant nucleic acid preparation, biochemical analysis, cell culture, and transgene incorporation like electroporation, lipofection and microinjection standard techniques are used.

The term "Alzheimer's tau" refers to the group of specifically truncated isoforms of tau protein engineered genetically that corresponds to those present exclusively in AD diseased brain. Alzheimer's tau is capable of inducing of NF activity on its own or in combination of other molecules in the brain. As used herein, the term Alzheimer's tau protein refers to the group of truncated tau forms present in AD-diseased human brain tissue.

The term "transgene" is used herein to describe genetic material, which has been artificially inserted into the genome of a cell, particularly a mammalian cell for implantation into a living animal. For specific countries, it may be necessary to specifically exclude certain subject matter from this aspect, such as human totipotent stem cells as such or processes which lead to such cells, falling under Art.6 (1) and (2) of the EC Directive 98/44/EC.

By "Alzheimer's disease" (abbreviated herein as "AD") is meant a condition associated with formation of neurofibrillary tangles and beta amyloid plaques, as well as impairment in both learning and memory. "AD" as used herein is meant to encompass both AD as well as AD-type pathologies, i.e., diseases of the central nervous system with symptoms similar to AD.

By "Neurofibrillary activity" (abbreviated herein as "INF" activity) is meant a condition associated with formation of neurofibrillary tangles in central nervous system with symptoms similar to AD.

By "symptoms similar to AD" and "phenomenon associated with AD" is meant a structural, molecular, or functional event associated with AD, particularly such an event that is readily assessable in an animal model. Such events include, but are not limited to, neurofibrillary pathology, learning and memory deficits, and other AD-associated characteristics.

By "transgenic animal" is meant a non-human animal, usually a mammal (e.g., a mouse, rat, rabbit, hamster, etc.), having a non-endogenous (i.e., heterologous) nucleic acid sequence present as an extrachromosomal element in a portion of its cell or stably integrated into its germ line DNA (i.e., in the genomic sequence of most or all of its cells). Heterologous nucleic acid is introduced into the germ line of such transgenic animals by genetic manipulation of, for example, embryos of the host animal.

By "construct" is meant a recombinant nucleic acid sequence, generally recombinant DNA sequences, operable linked to tissue specific or general promoter, which is generated for the purpose of the expression of a specific nucleotide sequence(s), in mammalian cells, or is to be used in the construction of other recombinant nucleotide sequences.

The present invention provides the structure, sequence and method for generating of DNA constructs used for transgenic animal preparation, which are characterised by the following features:

A DNA construct comprises a cDNA molecule coding for N- and C-terminally truncated tau molecules, wherein
  the molecules have truncated at least 30 nucleotides downstream of the start codon and truncated at least the 30 nucleotides upstream of the stop codon of the full length tau cDNA sequence coding for 4-repeat and 3-repeat tau protein, respectively, as given in Seq. accession number NM_173727 in GeneBank
  the minimally truncated tau core encompasses a protein fragment which is encoded by nucleotides nos 742-930(seq ID No. 9) (numbered according to tau protein isoform 43)
  said DNA constructs are coding for proteins, which have neurofibrillary (NF) pathology producing activity when expressed in brain cells of animals.
  This NF pathology producing activity can be quantified by counts of neurofibrillary tangles per selected brain region, e.g. using stereology approach. Alternatively, neurobehavioural tests can be used for reliable evaluation of cognitive scores in learning memory-addressing tasks.

Specifically preferred tau cDNA molecules according to the present invention comprise a nucleotide sequence selected from the group of SEQ ID NOs 1 to 14. The sequences are depicted in FIG. 1.

In a preferred embodiment of the invention, said cDNA molecules represent a group of N- and C-terminally double truncated cDNAs, which comprises the following nucleotide (Derivatives from 4-repeat tau (tau 43) are labeled R4 and derivatives from 3-repeat tau (tau 44) are labeled R3). Numbering used here is derived from full length tau cDNA described in Goedert et al.(24):

```
                                        SEQ ID NO: 1 (91-1059, R4)
ATGCACCAAGACCAAGAGGGTGACACGGACGCTGGCCTGAAAGCTGAAGAAGCAGGCATTG-
GAGACACCCCCAGCCTGGAAGACGAAGCTGCTGGTCACGTGACCCAAGCTCGCATGGT-
CAGTAAAAGCAAAGACGGGACTGGAAGCGATGACAAAAAAGCCAAGGGGGCTGATG-
GTAAAACGAAGATCGCCACACCGCGGGGAGCAGCCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAGATAATTAATAAGAAGCTGGATCT-
TAGCAACGTCCAGTCCAAGTGTGGCTCAAAGGATAATATCAAACACGTCCCGGGAGGCG-
GCAGTGTGCAAATAGTCTACAAACCAGTTGACCTGAGCAAGGTGACCTCCAAGTGTGGCT-
CATTAGGCAACATCCATCATAAACCAGGAGGTGGCCAGGTGGAAGTAAAACTGAGAAGCT-
```

-continued

TGACTTCAAGGACAGAGTCCAGTCGAAGATTGGGTCCCTGGACAATATCACCCACGTCCCTG-
GCGGAGGAAATAAAAAGATTGAAACCCACAAGCTGACCTTCCGCGAGAACGCCAAAGC-
CAAGACAGACCACGGGGCGGAGATCGTGTACAAGTCGCCAGTGGTGTCTGGG-
GACACGTCTCCACGGCATCTCAGCAATGTC

SEQ ID NO: 2 (205-999, R4)
ATGGTCAGTAAAAGCAAAGACGGGACTGGAAGCGATGACAAAAAAGCCAAGGGGGCTGATG-
GTAAAACGAAGATCGCCACACCGCGGGGAGCAGCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAGATAATTAATAAGAAGCTGGATCT-
TAGCAACGTCCAGTCCAAGTGTGGCTCAAAGGATAATATCAAACACGTCCCGGGAGGCG-
GCAGTGTGCAAATAGTCTACAAACCAGTTGACCTGAGCAAGGTGACCTCCAAGTGTGGCT-
CATTAGGCAACATCCATCATAAACCAGGAGGTGGCCAGGTGGAAGTAAAATCTGAGAAGCT-
TGACTTCAAGGACAGAGTCCAGTCGAAGATTGGGTCCCTGGACAATATCACCCACGTCCCTG-
GCGGAGGAAATAAAAAGATTGAAACCCACAAGCTGACCTTCCGCGAGAACGCCAAAGC-
CAAGACAGACCACGGGGCGGAG

SEQ ID NO: 3 (277-999, R4)
ATCGCCACACCGCGGGGAGCAGCCCCTCCAGGCCAGAAGGGCCAGGCCAACGCCACCAG-
GATTCCAGCAAAAACCCCGCCCGCTCCAAAGACACCACCCAGCTCTGGTGAACCTCCAAAAT-
CAGGGGATCGCAGCGGCTACAGCAGCCCCGGCTCCCCAGGCACTCCCGGCAGC-
CGCTCCCGCACCCCGTCCCTTCCAACCCCACCCACCCGGGAGCCCAAGAAGGTGGCAGTG-
GTCCGTACTCCACCCAAGTCGCCGTCTTCCGCCAAGAGCCGCCTGCAGACAGCCCCCGTGC-
CCATGCCAGACCTGAAGAATGTCAAGTCCAAGATCGGCTCCACTGAGAACCTGAAGCACCAGC-
CGGGAGGCGGGAAGGTGCAGATAATTAATAAGAAGCTGGATCTTAGCAACGTCCAGTCCAAGT-
GTGGCTCAAAGGATAATATCAAACACGTCCCGGGAGGCGGCAGTGTGCAAATAGTCTACAAAC-
CAGTTGACCTGAGCAAGGTGACCTCCAAGTGTGGCTCATTAGGCAACATCCATCATAAACCAG-
GAGGTGGCCAGGTGGAAGTAAAATCTGAGAAGCTTGACTTCAAGGACA-
GAGTCCAGTCGAAGATTGGGTCCCTGGACAATATCACCCACGTCCCTGGCGGAG-
GAAATAAAAAGATTGAAACCCACAAGCTGACCTTCCGCGAGAACGCCAAAGCCAAGACAGAC-
CACGGGGCGGAG

SEQ ID NO: 4 (205-1089, R4)
ATGGTCAGTAAAAGCAAAGACGGGACTGGAAGCGATGACAAAAAAGCCAAGGGGGCTGATG-
GTAAAACGAAGATCGCCACACCGCGGGGAGCAGCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAGATAATTAATAAGAAGCTGGATCT-
TAGCAACGTCCAGTCCAAGTGTGGCTCAAAGGATAATATCAAACACGTCCCGGGAGGCG-
GCAGTGTGCAAATAGTCTACAAACCAGTTGACCTGAGCAAGGTGACCTCCAAGTGTGGCT-
CATTAGGCAACATCCATCATAAACCAGGAGGTGGCCAGGTGGAAGTAAAATCTGAGAAGCT-
TGACTTCAAGGACAGAGTCCAGTCGAAGATTGGGTCCCTGGACAATATCACCCACGTCCCTG-
GCGGAGGAAATAAAAAGATTGAAACCCACAAGCTGACCTTCCGCGAGAACGCCAAAGC-
CAAGACAGACCACGGGGCGGAGATCGTGTACAAGTCGCCAGTGGTGTCTGGG-
GACACGTCTCCACGGCATCTCAGCAATGTCTCCTCCACCGGCAGCATCGACATGGTAGAC

SEQ ID NO: 5 (277-1089, R4)
ATCGCCACACCGCGGGGAGCAGCCCCTCCAGGCCAGAAGGGCCAGGCCAACGCCACCAG-
GATTCCAGCAAAAACCCCGCCCGCTCCAAAGACACCACCCAGCTCTGGTGAACCTCCAAAAT-
CAGGGGATCGCAGCGGCTACAGCAGCCCCGGCTCCCCAGGCACTCCCGGCAGC-
CGCTCCCGCACCCCGTCCCTTCCAACCCCACCCACCCGGGAGCCCAAGAAGGTGGCAGTG-
GTCCGTACTCCACCCAAGTCGCCGTCTTCCGCCAAGAGCCGCCTGCAGACAGCCCCCGTGC-
CCATGCCAGACCTGAAGAATGTCAAGTCCAAGATCGGCTCCACTGAGAACCTGAAGCACCAGC-
CGGGAGGCGGGAAGGTGCAGATAATTAATAAGAAGCTGGATCTTAGCAACGTCCAGTCCAAGT-
GTGGCTCAAAGGATAATATCAAACACGTCCCGGGAGGCGGCAGTGTGCAAATAGTCTACAAAC-
CAGTTGACCTGAGCAAGGTGACCTCCAAGTGTGGCTCATTAGGCAACATCCATCATAAACCAG-
GAGGTGGCCAGGTGGAAGTAAAATCTGAGAAGCTTGACTTCAAGGACA-
GAGTCCAGTCGAAGATTGGGTCCCTGGACAATATCACCCACGTCCCTGGCGGAG-
GAAATAAAAAGATTGAAACCCACAAGCTGACCTTCCGCGAGAACGCCAAAGCCAAGACAGAC-
CACGGGGCGGAGATCGTGTACAAGTCGCCAGTGGTGTCTGGGGACACGTCTCCACGGCATCT-
CAGCAATGTCTCCTCCACCGGCAGCATCGACATGGTAGAC

SEQ ID NO: 6 (715-999, R4)
ATCAAACACGTCCCGGGAGGCGGCAGTGTGCAAATAGTCTACAAACCAGTTGACCTGAGCAAG-
GTGACCTCCAAGTGTGGCTCATTAGGCAACATCCATCATAAACCAGGAGGTGGCCAGGTG-
GAAGTAAAATCTGAGAAGCTTGACTTCAAGGACAGAGTCCAGTCGAAGATTGGGTCCCTG-
GACAATATCACCCACGTCCCTGGCGGAGGAAATAAAAAGATTGAAACCCACAAGCT-
GACCTTCCGCGAGAACGCCAAAGCCAAGACAGACCACGGGGCGGAG

SEQ ID NO: 7 (709-999, R4)
GATAAATATCAAACACGTCCCGGGAGGCGGCAGTGTGCAAATAGTCTACAAACCAGTTGACCT-
GAGCAAGGTGACCTCCAAGTGTGGCTCATTAGGCAACATCCATCATAAACCAGGAGGTGGC-
CAGGTGGAAGTAAAATCTGAGAAGCTTGACTTCAAGGACAGAGTCCAGTCGAAGATTGG-
GTCCCTGGACAATATCACCCACGTCCCTGGCGGAGGAAATAAAAAGATTGAAACCCACAAGCT-
GACCTTCCGCGAGAACGCCAAAGCCAAGACAGACCACGGGGCGGAG

SEQ ID NO: 8 (715-954, R4)
ATCAAACACGTCCCGGGAGGCGGCAGTGTGCAAATAGTCTACAAACCAGTTGACCTGAGCAAG-
GTGACCTCCAAGTGTGGCTCATTAGGCAACATCCATCATAAACCAGGAGGTGGCCAGGTG-
GAAGTAAAATCTGAGAAGCTTGACTTCAAGGACAGAGTCCAGTCGAAGATTGGGTCCCTG-
GACAATATCACCCACGTCCCTGGCGGAGGAAATAAAAAGATTGAAACCCACAAGCTG

SEQ ID NO: 9 (742-930, R4)
GTGCAAATAGTCTACAAACCAGTTGACCTGAGCAAGGTGACCTCCAAGTGTGGCTCATTAG-
GCAACATCCATCATAAACCAGGAGGTGGCCAGGTGGAAGTAAAATCTGAGAAGCT-
TGACTTCAAGGACAGAGTCCAGTCGAAGATTGGGTCCCTGGACAATATCACCCACGTCCCTG-
GCGGAGGAAAT

SEQ ID NO: 10 (91-966, R3)
ATGCACCAAGACCAAGAGGGTGACACGGACGCTGGCCTGAAAGCTGAAGAAGCAGGCATTG-
GAGACACCCCCAGCCTGGAAGACGAAGCTGCTGGTCACGTGACCCAAGCTCGCATGGT-
CAGTAAAAGCAAAGACGGGACTGGAAGCGATGACAAAAAAGCCAAGGGGGCTGATG-
GTAAAACGAAGATCGCCACACCGCGGGGAGCAGCCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAAATAGTCTACAAACCAGTTGACCTGAGCAAGGT-
GACCTCCAAGTGTGGCTCATTAGGCAACATCCATCATAAACCAGGAGGTGGCCAGGTG-
GAAGTAAAATCTGAGAAGCTTGACTTCAAGGACAGAGTCCAGTCGAAGATTGGGTCCCTG-
GACAATATCACCCACGTCCCTGGCGGAGGAAATAAAAAGATTGAAACCCACAAGCT-
GACCTTCCGCGAGAACGCCAAAGCCAAGACAGACCACGGGGCGGAGATCGTGTACAAGTCGC-
CAGTGGTGTCTGGGGACACGTCTCCACGGCATCTCAGCAATGTC

SEQ ID NO: 11 (205-906, R3)
ATGGTCAGTAAAAGCAAAGACGGGACTGGAAGCGATGACAAAAAAGCCAAGGGGGCTGATG-
GTAAAACGAAGATCGCCACACCGCGGGGAGCAGCCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAAATAGTCTACAAACCAGTTGACCTGAGCAAGGT-
GACCTCCAAGTGTGGCTCATTAGGCAACATCCATCATAAACCAGGAGGTGGCCAGGTG-
GAGGTAAAATCTGAGAAGCTTGACTTCAAGGACAGAGTCCAGTCGAAGATTGGGTCCCTG-
GACAATATCACCCACGTCCCTGGCGGAGGAAATAAAAAGATTGAAACCCACAAGCT-
GACCTTCCGCGAGAACGCCAAAGCCAAGACAGACCACGGGGCGGAG

SEQ ID NO: 12 (277-906, R3)
ATCGCCACACCGCGGGGAGCAGCCCCTCCAGGCCAGAAGGGCCAGGCCAACGCCACCAG-
GATTCCAGCAAAAACCCCGCCCGCTCCAAAGACACCACCCAGCTCTGGTGAACCTCCAAAAT-
CAGGGGATCGCAGCGGCTACAGCAGCCCCGGCTCCCCAGGCACTCCCGGCAGC-
CGCTCCCGCACCCCGTCCCTTCCAACCCCACCCACCCGGGAGCCCAAGAAGGTGGCAGTG-
GTCCGTACTCCACCCAAGTCGCCGTCTTCCGCCAAGAGCCGCCTGCAGACAGCCCCCGTGC-
CCATGCCAGACCTGAAGAATGTCAAGTCCAAGATCGGCTCCACTGAGAACCTGAAGCACCAGC-
CGGGAGGCGGGAAGGTGCAAATAGTCTACAAACCAGTTGACCTGAGCAAGGTGACCTCCAAGT-
GTGGCTCATTAGGCAACATCCATCATAAACCAGGAGGTGGCCAGGTGGAAGTAAAATCT-
GAGAAGCTTGACTTCAAGGACAGAGTCCAGTCGAAGATTGGGTCCCTGGACAATATCAC-

-continued
CCACGTCCCTGGCGGAGGAAATAAAAAGATTGAAACCCACAAGCTGACCTTCCGCGAGAACGC-
CAAAGCCAAGACAGACCACGGGGCGGAG SEQ ID NO: 13 (205-996, R3)
ATGGTCAGTAAAAGCAAAGACGGGACTGGAAGCGATGACAAAAAAGCCAAGGGGCTGATG-
GTAAAACGAAGATCGCCACACCGCGGGGAGCAGCCCCTCCAGGCCAGAAGGGCCAGGC-
CAACGCCACCAGGATTCCAGCAAAAACCCCGCCCGCTCCAAAGACACCACCCAGCTCTGGT-
GAACCTCCAAAATCAGGGGATCGCAGCGGCTACAGCAGCCCCGGCTCCCCAGGCACTCCCG-
GCAGCCGCTCCCGCACCCCGTCCCTTCCAACCCCACCCACCCGGGAGCCCAAGAAGGTG-
GCAGTGGTCCGTACTCCACCCAAGTCGCCGTCTTCCGCCAAGAGCCGCCTGCAGACAGC-
CCCCGTGCCCATGCCAGACCTGAAGAATGTCAAGTCCAAGATCGGCTCCACTGAGAACCT-
GAAGCACCAGCCGGGAGGCGGGAAGGTGCAAATAGTCTACAAACCAGTTGACCTGAGCAAGGT-
GACCTCCAAGTGTGGCTCATTAGGCAACATCCATCATAAACCAGGAGGTGGCCAGGTG-
GAAGTAAAATCTGAGAAGCTTGACTTCAAGGACAGAGTCCAGTCGAAGATTGGGTCCCTG-
GACAATATCACCCACGTCCCTGGCGGAGGAAATAAAAAGATTGAAACCCACAAGCT-
GACCTTCCGCGAGAACGCCAAAGCCAAGACAGACCACGGGGCGGAGATCGTGTACAAGTCGC-
CAGTGGTGTCTGGGGACACGTCTCCACGGCATCTCAGCAATGTCTCCTCCACCG-
GCAGCATCGACATGGTAGAC SEQ ID NO: 14 (277-996, R3)
ATCGCCACACCGCGGGGAGCAGCCCCTCCAGGCCAGAAGGGCCAGGCCAACGCCACCAG-
GATTCCAGCAAAAACCCCGCCCGCTCCAAAGACACCACCCAGCTCTGGTGAACCTCCAAAAT-
CAGGGGATCGCAGCGGCTACAGCAGCCCCGGCTCCCCAGGCACTCCCGGCAGC-
CGCTCCCGCACCCCGTCCCTTCCAACCCCACCCACCCGGGAGCCCAAGAAGGTGGCAGTG-
GTCCGTACTCCACCCAAGTCGCCGTCTTCCGCCAAGAGCCGCCTGCAGACAGCCCCCGTGC-
CCATGCCAGACCTGAAGAATGTCAAGTCCAAGATCGGCTCCACTGAGAACCTGAAGCACCAGC-
CGGGAGGCGGGAAGGTGCAAATAGTCTACAAACCAGTTGACCTGAGCAAGGTGACCTCCAAGT-
GTGGCTCATTAGGCAACATCCATCATAAACCAGGAGGTGGCCAGGTGGAAGTAAAATCT-
GAGAAGCTTGACTTCAAGGACAGAGTCCAGTCGAAGATTGGGTCCCTGGACAATATCAC-
CCACGTCCCTGGCGGAGGAAATAAAAAGATTGAAACCCACAAGCTGACCTTCCGCGAGAACGC-
CAAAGCCAAGACAGACCACGGGGCGGAGATCGTGTACAAGTCGCCAGTGGTGTCTGGG-
GACACGTCTCCACGGCATCTCAGCAATGTCTCCTCCACCGGCAGCATCGACATGGTAGAC The truncated tau sequences may be adapted due to the specific host cell whereto the construct is transferred (codon usage, codon preferences, homolog adaptations (exchanging one or more of the human codons with the host cell codon, if differences are present).

Preferred Features of the Constructs:

The above cDNA sequences are linked to regulatory sequences in order to drive an expression of truncated tau protein in the brain. Modification of Thy-1 gene (25) was performed in such a way that regulatory sequence, which directs an expression into T-cells was deleted and truncated cDNA sequence was introduced in between Spe-I and Xho-restriction sites. The modified construct was stripped of prokaryotic sequences and introduced into male pronucleus via microinjection. Any functional promoters or promoter-enhancer complexes may be used for expression of above described truncated tau cDNAs.

According to another aspect, the present invention provides a method for the preparation and testing of molecules according to the present invention, characterized by the following steps:

(a) construction of a recombinant prokaryotic cloning plasmids carrying coding sequences for a double truncated tau molecule with deletions covering at least the first first 30 and the last 30 nucleotides of three or four repeat tau cDNA molecules,
(b) construction of an eukaryotic expression plasmid carrying appropriate promoters for brain expression or ubiquitous expression and respective cDNA sequences of truncated tau molecules and the combination thereof,
(c) growing bacteria containing said plasmids and amplification, of the plasmids and their extraction in high quantity,
(d) transfection of said gene constructs into COS-7 cells and their analysis using western blot technique,
(e) isolation and purification of the gene construct such that all prokaryotic sequences are excluded, and dilution of transgenes in a buffer in concentration suitable for microinjection (see Example 1),
(f) verification of gene constructs intended for microinjection.

This is performed by restriction analysis, gene sequencing and protein analysis after transient transfections into mammalian cells after which the correct size of proteins and their reactivity with specific monoclonal antibodies were evaluated (see Example 1, FIG. 2.b).

The present invention therefore provides a transgenic non-human animal of whose germ and/or somatic cells comprise the DNA construct encoding for Alzheimer's tau protein, which can be used as a suitable animal model of Alzheimer's disease.

It is therefore an object of the present invention to provide a transgenic non-human animal all of whose germ and/or somatic cells comprises the human truncated tau cDNA molecules. Cloned human Alzheimer's tau cDNA sequence is linked to a promoter sequence, which directs the expression of Alzheimer's tau in tissue specific manner or ubiquitously.

Transgenic animals of the invention are engineered using well known regular procedures of microinjection, into the male pronucleus of one day old fertile embryos of rats. The transgenes can be introduced into embryonic cells also by other methods known in the art, including transfection, lipofection, electroporation and with the help of retroviruses or by other means. Embryos carrying the transgene can then be implanted into pseudopregnant animals.

It is therefore an object of invention to provide a method for genotyping of newborn animals. PCR analysis using specific oligonucleotides that allow an amplification of targent sequences of the transgene is therefore employed for this purpose. Oligonucleotides used for genotyping were designed in a way that the transcription initiation site of the transgene including the ATG codon and Kozak sequence could be verified eventually by DNA sequencing of the PCR product (primer pair A). Moreover one primer was anneals to the heterogeneous promoter and another primer anneals to nucleotide sequence coding for Alzheimer's tau protein. Similar designing criteria were applied for the stop codon (primer pair B). Integrity of the transgene therefore can be monitored this way. Sequences of the diagnostic oligonucleotides are therefore as follows:

Primer pair A:

```
                                         (SEQ ID NO: 16)
Sense:      5'-GTGGATCTCAAGCCCTCAAG-3'

(SEQ ID NO: 17)
Antisense:  5'-GATCCCCTGATTTTGGAGGT-3'
```

Expected size of PCR product is 235 nucleotides.
Primer pair B:

```
                                         (SEQ ID NO: 18)
Sense:      5'-AAGGTGACCTCCAAGTGTGG-3'

(SEQ ID NO: 17)
Antisense:  5'-GGTATGCATGGAGGGAGAAG-3'
```

Expected size of PCR product is 438 nucleotides.

Presence of the PCR fragment is therefore specific to animals with transgene integrated in the genome (see Example 2)

The founder animals can be used for breeding with wild-type animals to produce F1 generation of animals, which are heterozygous for the transgene. In further embodiments, these heterozygous animals can be interbred to obtain the viable transgenic embryos whose somatic and germ cells are homozygous for the genes coding for Alzheimer's tau protein.

Another object of the present invention is to provide non-human animals of which germ and somatic cells transiently or stably express said DNA construct coding for Alzheimer's tau protein and exhibiting NF pathology in the brain. The preferred animal of this invention is a rat, wherein the protein encoded by said DNA molecules is expressed in the brain.

The most preferred embodiment of the present invention is a transgenic non-human animal wherein the Alzheimer's tau protein encoded by said DNA molecules is expressed in the brain of the animal. The expression of Alzheimer's tau was detected by several monoclonal antibodies as described in Example 3 and documented on FIG. 3. Expression of the protein in different brain regions of transgenic lineage is documented on FIG. 4.

The present invention therefore provides a transgenic non-human animal wherein DNA molecules coding for Alzheimer's tau protein are stably integrated in the genome of said animals or otherwise present in the cell nucleus in order to be transcribed. Said animals are characterized by the following features:

transgenes are transmitted to subsequent generations of animals according to Mendelian laws forming a transgenic lineage (see Example 4)
the inherited transgene is expressing truncated proteins in brains of the founder animals and the progeny as shown in Example 3 FIG. 4.

The present invention therefore provides the transgenic non-human animals, which exhibit neurofibrillary pathology in the central nervous system (CNS). Said animals are characterized by the following features:

Expression of truncated tau proteins promotes the formation of neurofibrillary pathology (Example 5)
PHF 1 immunoreactive NFTs showed that endogenous normal rat tau participate on the formation of NFTs (Example 5)
Neurofibrillary tangles are present as intracellular inclusions and filaments in the neurons of CNS and are homologous to NFT in human AD diseased brains.
Immunofluorescence revealed the presence of small-rod like structures similar to those observed in pre-clinical Alzheimer's disease-observed in human brain tissue (see Example 5).

In the preferred embodiment of the invention, transgenic animals display such neuropathology as neurofibrillary tangles, ghost tangles and neuropil threads that are formic acid sensitive. Neurofibrillary tangles are composed of an abnormal accumulation of intraneuronal filaments. The tangle components are comprised from Alzheimer's tau as well as normal tau molecules. Such transgenic animals serve as suitable model system for study of Alzheimer's disease and development of therapeutic, preventive and diagnostic substances.

The invention provides a transgenic animal developing NF pathology, and having a genetic background allowing induction of risk factors associated with AD, thereby representing a disease model for humans.

The present invention therefore provides a transgenic non-human animal, wherein the genetic background, in which DNA molecules are stably integrated in the genome of spontaneously hypertensive animal or otherwise present in the cell nucleus in order to be transcribed within the specific genetic background.

Another aspect of the invention is to provide an animal model comprising the combination of genetic factors and other risk factors associated with AD as follows:

hypertension which is the most common risk factors of AD,
diabetes which can be induced by diet (diabetes is important risk factor of AD),
hypercholestrolemia which can be induced by diet (another important risk factor of AD).

Said pathological situations can easily be induced in the provided animal model. Suitable examples were previously reported in literature (e.g. in 26, 27, 28).

Moreover the provided animal model is the first animal model, which expresses neurofibrillary pathology on the genetic background of SHR.

According to another aspect the present invention provides an animal, which represents an experimental model of sporadic Alzheimer's disease, said model permits an assessment of the role of risk factors associated with AD development. Risk factors play a critical role in the vast majority of AD cases, the model may therefore be considered as a model of sporadic AD which represents 90% of all cases of AD neurodegenerations.

In another preferred embodiment, the present invention provides a screening assay system for substances for the treatment prevention and diagnosis of Alzheimer's disease, which comprises:

evaluation of substances by:
detecting changes of neurofibrillary pathology in said animals
measuring of neurobehavioural changes in transgenic animals
measuring of the cognitive score in transgenic animals
biochemical measuring of AD specific markers in animal tissues and body fluids a validation system for substances for the treatment and prevention of tauopathies preferably AD a validation system for the development of diagnostic markers and probes for the detection tauopathies, preferably AD a validation system for substances for treatment of hypertension, diabetes, dislipidaemia and hypercholesterolemia in combination with tauopathies preferably AD The present invention therefore provides an in-vivo assay to assess the efficacy of substances, or therapies in particular NFT reducing or preventing therapies. The animals can be used for screening of substances or therapies for neurodegenerative diseases, in particular tauopathies, preferably AD and other neurodegenerative diseases accompanied by neurofibrillary tangles formation.

Therefore the present invention provides a model system consisting of transgenic animals, cells and assays that are useful in the study of the etiology and treatment of Alzheimer's disease. The assays are also useful for screening for substances that inhibit the formation of neurofibrillary pathology and other therapeutic effects of the substances.

The transgenic animals of the present invention and animal cells derived thereof are used for screening compounds for a potential effect in the treatment of Alzheimer's disease using standard methodologies. The compound is administered to the animals or introduced into the culture media over a period of time and in various dosages, then the animals or animal cells are examined for alterations in histopathology and Alzheimer's tau expression respectively. Furthermore, the ability to perform neurobehavioural testing to the transgenic animals enables cognitive function to be monitored following treatment with potential therapeutic agents. Screening of compounds leads to the selection of specific agents for the prevention or treatment or diagnosis of Alzheimer's disease. Many variations of screening methods are known to those skilled in the art and may be applied within the scope of the present invention.

The transgenic animal model of the present invention may also be used to unravel the molecular cascade of events leading to neurodegeneration and Alzheimer's disease such that therapeutic targets may be identified.

Still another aspect of the invention is to provide an in vitro assay based on cell lines derived from a transgenic animal or cell line derived from a transgenic rat embryo of the present invention, where the said assay is employed as a screening and validation tool for the discovery and development of Alzheimer's diagnosis and markers. Said in vitro assay is based on the cell lines and may also be employed as a screening and validation tool for the discovery of anti Alzheimer's therapeutic and preventive drugs.

The following examples are presented by the way of illustration and, because various other embodiments will be apparent to those in the art, the following is not to be construed as a limitation on the scope of the invention.

BRIEF DESCRIPTION OF THE FIGURES

FIG. 1 Scheme of Alzheimer's tau protein cDNAs employed for engineering of gene expression constructs, which were used in production of transgenic animals of the present invention.

Primary cultures of transgenic and nontransgenic rat neurons can be used for this purpose after in vitro cultivation and effect of the drug candidates on the mitochondrial transport can be evaluated using videomicroscopy. Cortical (Cx) and and hippocampal (Hipp) neurons loaded with vital dye (e.g. Mito-trek) are shown after 3 days in vitro cultivation (3DIV). Mitochondria (MT) are visualized.

Figure 10:
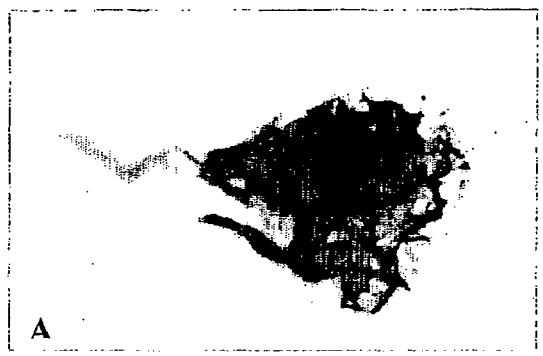
Figure 10:
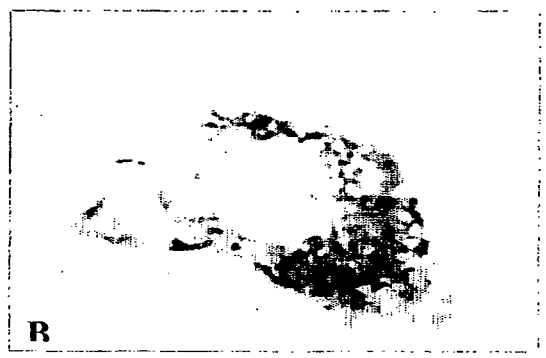
Figure 10:
Figure 10:
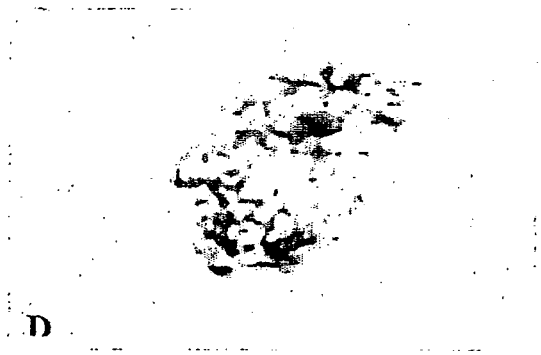
Figure 10:
Figure 10:
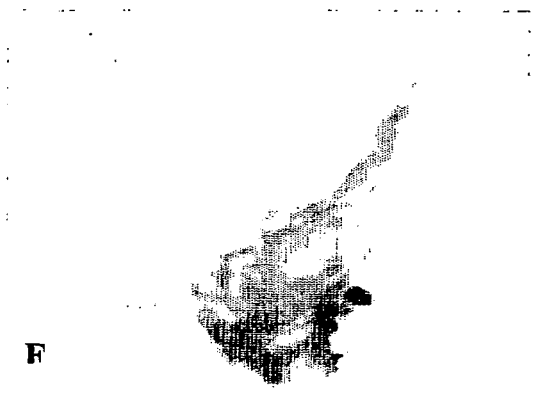

FIG. 10 Histophathological features of Alzheimer's disease, recapitulated in transgenic animal of present invention. Presented neurofibrillary pathology is one of the major hallmark of Alzheimer's disease. FIG. 10 shows a comparison of neurofibrillary tangles detected by Gallyas silver technique (A, C) and also by immunohistochemistry (E) in AD diseased human brain, to the equivalent pathological structures observed in transgenic animal of present invention. Immunochemical staining was performed with monoclonal antibody 7.51 which recognizes generic tau epitope in the tandem repeat region (29).

EXAMPLES

Example 1

Figure 2:
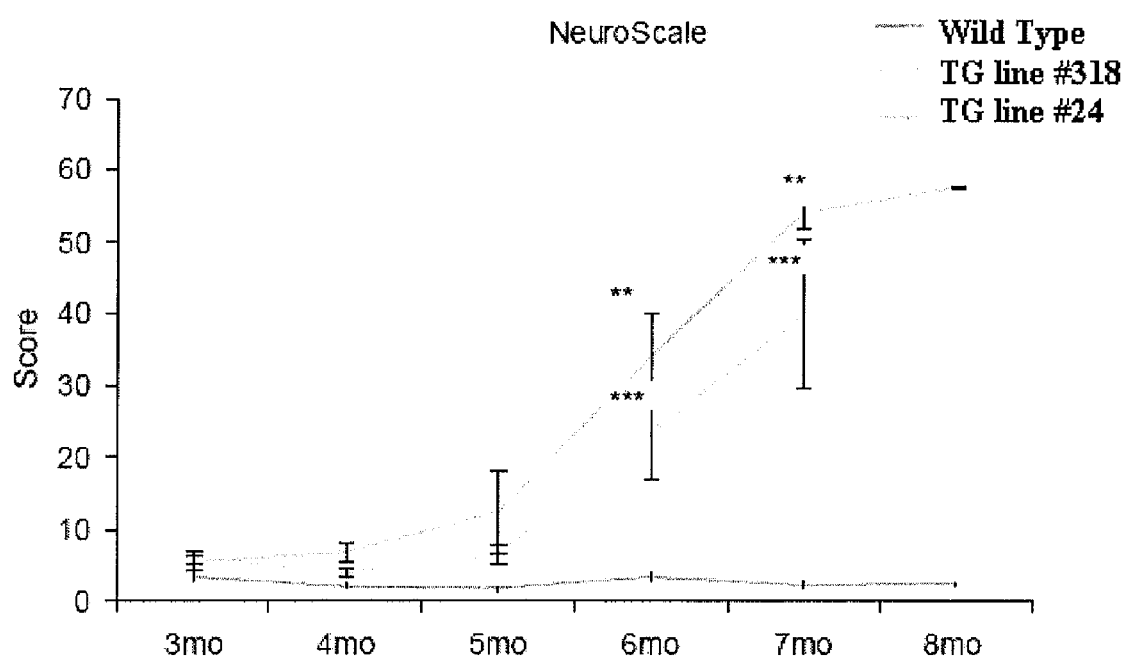
FIG. 2 Preparation and verification of gene constructs used for the production of transgenic animals. Construction of transgenic animals was performed via pronuclear microinjection of cloned gene constructs containing coding sequence for Alzheimer's tau. Gene constructs were verified by restriction analysis and PCR using transgene specific primers (panel A, agarose gel of PCR amplified and DNA fragment) as well as by DNA sequencing in order to control for potential mutations. Verification was followed by purification of gene constructs (panel B, agarose gel of pure transgene fragment) and transient transfections into mammalian cells (panel C, Western blot verification of protein expression). After the assays were completed the constructs were stripped of prokaryotic sequences and injected into one-day old rat embryos. The bottom flow chart shows a simplified procedure of transgenic animals production.

Design of Gene Constructs Containing DNA Sequence Coding for Alzheimer's Tau Protein—Human Truncated Tau Gene; Engineering and Verification of Gene Constructs for Ubiquitous and Tissue Specific Expression in Transgenic Animals Construction of Alzheimer's tau expression vectors consist of procedures that include:
  design of coding sequence especially deletions and truncations are shown in FIG. 1.
  these portions of tau gene were PCR amplified with the help of proofreading DNA polymerase and oligonucleotides equipped with appropriate restriction sequences, so that they can be cloned under general or tissue specific promoters in an eukaryotic expression vector, cloning was performed using standard procedures in a common bacterial strains
  verification of cloned genes was performed in order to check directionality of the inserted gene which was confirmed by restriction digestions and or PCR analysis (FIG. 2A). In addition, the constructs were partially sequenced to exclude the possible mutated forms
  purification of fragment intended for microinjection (FIG. 2B)
  verification of protein expression using transfections of transgene into mammalian cells, mainly COS-7 and C6 rat glioma cells, and analysis of expression of proteins in a eukaryotic cells by western blot method (FIG. 2C).

All the methods are described in a manual: Sambrook et al., Molecular Cloning, A Laboratory Manual, Cold Spring Harbor Laboratory Press, 1989 (14).

Example 2

Production of Transgenic Rat

Cloned gene construct containing Alzheimer's tau coding sequence was injected into male pronucleus of one day old embryos. Fertilized eggs were extracted from SHR donor females in separate experiments using routine techniques (15). After microinjecting of DNA, the zygotes were in vitro cultured in $CO_2$ incubator for about 12 hours and implanted into oviductus of pseudopregnant foster mothers. Founders were identified by PCR of transgene specific target sequence from genomic DNA. To determine the tau genotypes, genomic DNA was purified from about 0.5 cm of tail taken from each rat. PCR analysis, was used to identify offspring which contained the transgene. Oligonucleotides for diagnostic PCR screening were designed in such a way that integrity of the transgene could be easily determined. For determination of number of transgene copies integrated in rat genome a real time PCR analysis was used.

For example Tg line #318 contained 4 copies of the transgene, which was determined by real time PCR using Sybre Green method and BioRad PCR machine.

Example 3

Genotyping of Animals Born After Embryo Implantation into Foster Mothers, Identification of Transgenic Animals and Assessment of Transmission of the Transgene to Subsequent Generations DNA extracted from tail tips: Genomic DNA was extracted by DNeasy tissue kit, Qiagen.

Figure 3:
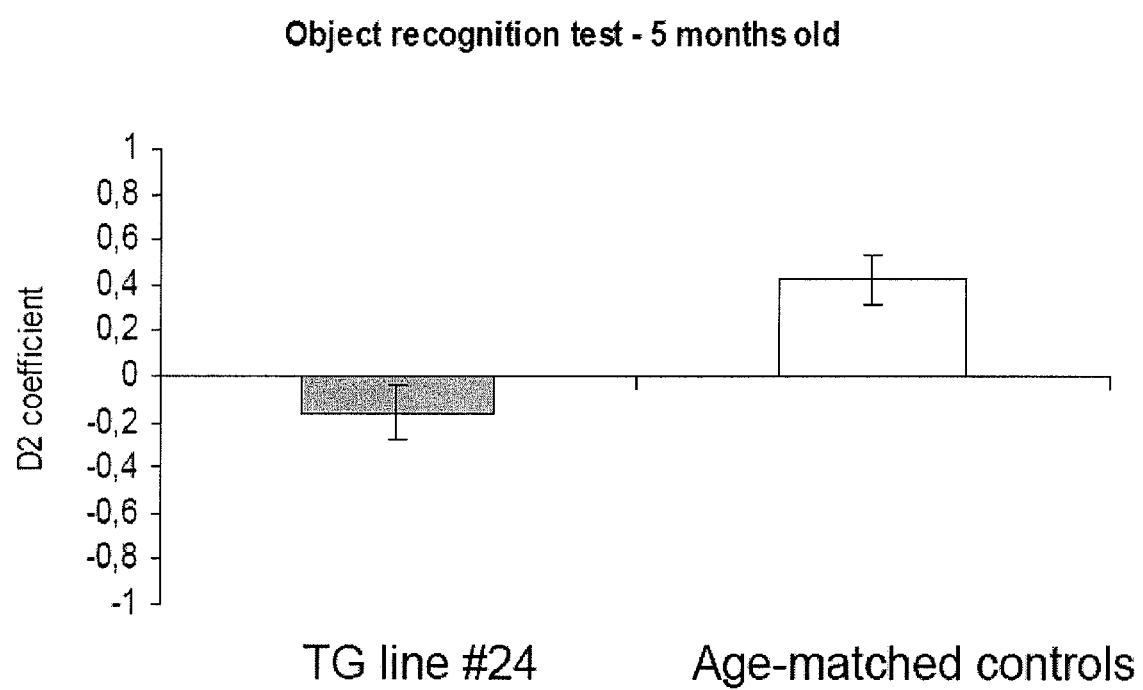
FIG. 3 Genotyping of transgenic founder animals and F1 generation of transgenic animals. Panel "A" shows controls for the genotyping experiment (+C, positive control; NAC, no amplification control; NTC, no template control). Panel "B" shows results of PCR genotyping. Sample number 12 represents a transgene positive animal Panel "C" outlines the breeding experiments performed to confirm founder animals. Furthermore the panel shows transgenic line of the present invention that has transmitted the transgene to the subsequent generations according to Mendelian laws.

Genotyping: Specific amplification of transgenes encoding double truncated tau forms was performed on genomic DNA derived from the parental generation of transgenic animals and is shown in FIGS. 3A and 3B. Further analysis of genomic DNA of the F1 generation revealed that transgenes are heritable since they were also identified in the offspring of parental generation. Transgenes encoding Alzheimer's tau are therefore fixed in chromosomal DNA of the animals. Genotyping was performed with two positive (plasmid and TG positive genomic DNA) and two negative controls (no amplification control heterologous genomic DNA; no template control for control of chemicals) as it is shown in FIG. 3A.

Analysis of transgene expression: Expression of mRNA derived from the transgenes were assessed by RT-PCR analysis, applying generally known methods including RT-PCR and agarose gel electrophoresis. RNA was extracted from flash frozen tissue of transgenic animals and subjected to reverse transcription followed by specific amplification of the cDNA.

Rat breeding and generation of heterozygous and homozygous rats: Transgene positive rats were bred to wild-type SHR. Germline transmission was achieved in several lines. In this example Tg line #318 is shown. Male and female transgenic rat, each of which contained four copies of the truncated human tau protein gene were mated with each other and wild type SHR rat to expand transgenic colony. Mendelian splitting ratios of transgene in the offspring were observed (FIG. 3C).

The transgenic animals of the present invention can be used to cross breed with transgenic animals overexpressing the human APP containing familial Alzheimer's disease (FAD) mutation or PS1 (13). The resulting rat will express both APP and PS1 with or without FAD mutation on hypertensive genetic background. The effect of PS1 and APP on NFT formation can be studied both in vivo and in vitro. Specifically, the onset and severity of AD-related pathologies can be examined by means of immounhistochemistry.

Example 4

Expression of Alzheimer's Tau Protein in the Brain of Transgenic Rats

Protein expression was performed using western blot analysis employing tau protein specific monoclonal antibodies. We have analysed brain tissues of rats that were geneticaly positive for transgene and were able to transmit the transgene to subsequent generations. Experiments were controled by simultaneous analysis of brain extracts from transgene negative age matched rats and transgene negative littermates.

Tissue sample preparation: approximately 2 mg of freshly isolated brain tissue was mechanically homogenized in 30 µl modified Hunt's lysis buffer (20 mM Tris, pH 8.0, 100 mM NaCl, 1 mM EDTA, 0.5% Igepal CA630, 0.5% Triton X-100), which contained protease inhibitor mix Complete-EDTA free (Roche). 170 µl of lysis buffer were added, homogenate was triturated with syringe and needle (22G) and frozen in liquid nitrogen. After slow thawing on ice, lysate was sonicated and centrifuged 15 minutes, 10000 g at +4° C. Protein content in samples was determined by Bradford assay using Beckman spectrophotometer.

Figure 4:
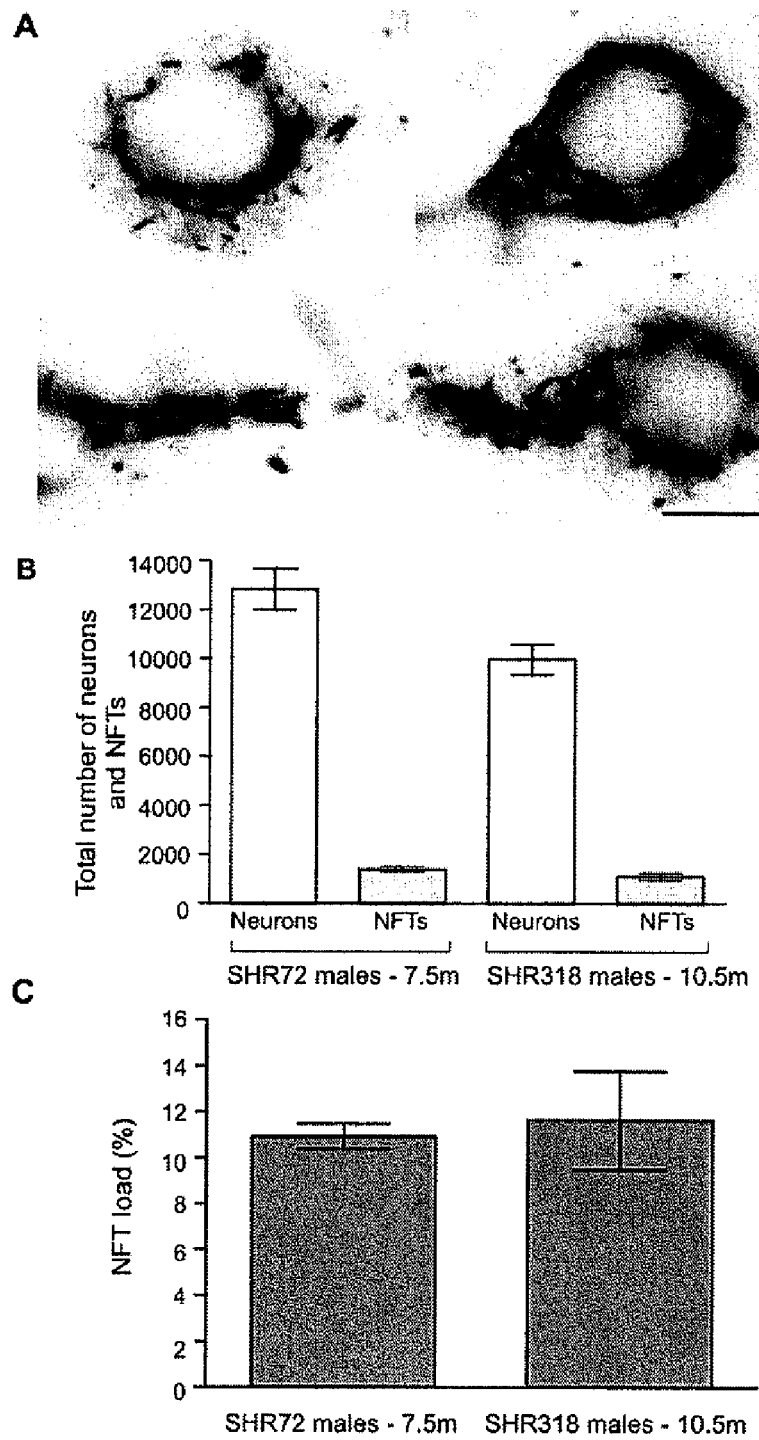
FIG. 4 Expression of Alzheimer's tau protein in brain of transgenic rat. The left panel represents a Western blot analysis and right panel is presenting total amount of proteins loaded per lane. Alzheimer's tau protein migrates at the size of 35 kD (lane 1, arrow), detected by pan-tau monoclonal antibody DC25. For Western blot an ECL technique was employed, and specific signal was observed after 1 min exposure. The 7.5 ug of total protein extract from brain lysates of transgenic animal was loaded (lane 1) whereas 25 ug of proteins was loaded from wild type control animals. M, molecular size marker.
Figure 5:
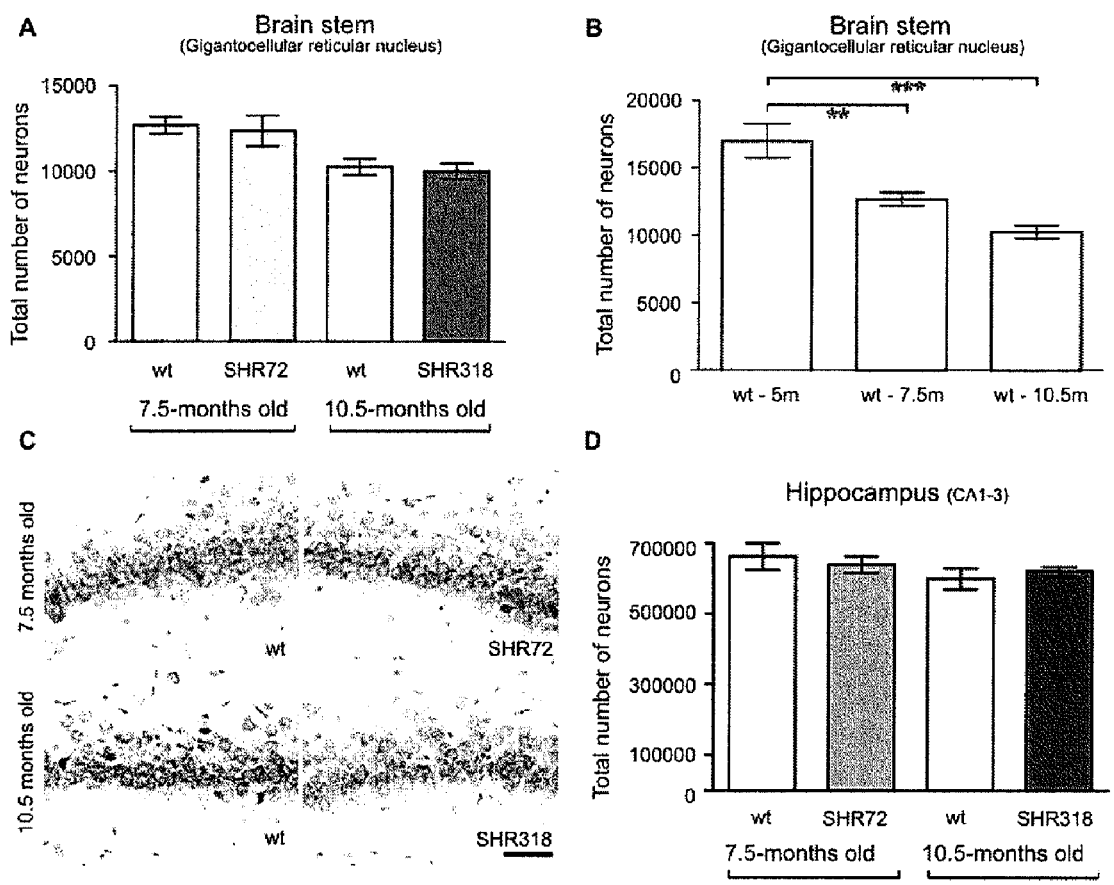
FIG. 5 Expression of Alzheimer's tau protein in different brain regions of transgenic rat. Western blot analysis of total protein lysates from transgenic rat brain regions. Lane 1, complete brain lysate of founder animal (generation F0)—10 ug proteins; lane 2, total brain lysate of transgenic animal of F2 generation; lanes 3-6, protein lysates from transgenic animal of F2 generation: 3—hippocampus, 4—subcortical area, 5—cerebral cortex, 6—spinal cord and medulla; lane 7-8 represent brain lysates from control non-transgenic littermates of F2 generation: 7—cortex, 8—cerebellum (Total protein load per lanes 2-8 was 20 ug).
Figure 6:
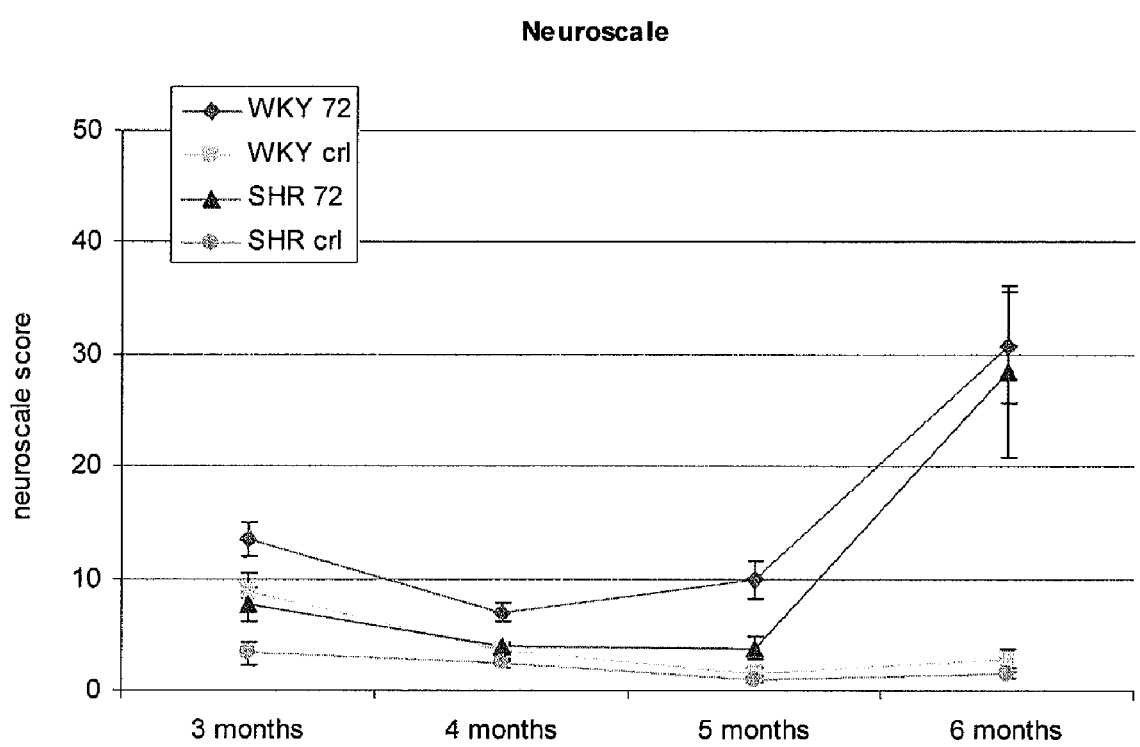
FIG. 6 Silver staining of brain sections from transgenic animal and nontransgenic control wild type animal. Intracellular inclusions and neurofibrillary filaments were detected in the neurons of the CNS of transgenic rat, (panel B and C, transgenic animal). Wild type rats do not show these structures in the homologous brain area (A, wild type control). Magnification: 200× (A and B), 400× (C)
Figure 7:
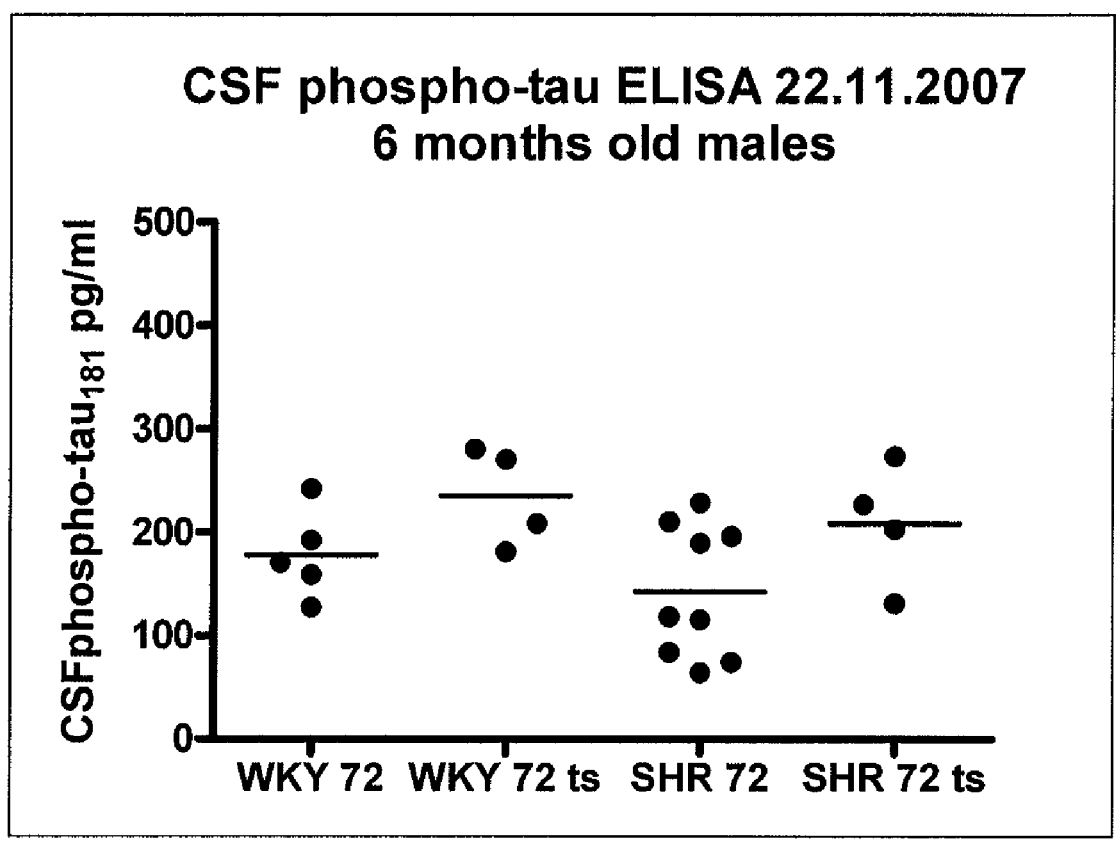
FIG. 7 Detection of neurofibrillary tangles using the pan-tau monoclonal antibody DC 25 in central nervous system of transgenic animal. mAb DC25 recognizes NFTs in the neurons of AD patients. The equivalent structures are recognized in the brain of transgenic rat (panel B and D). Wild type rats did not show any similar structures in the homologous brain area, (A, C). Magnification: 100× (A, B), 200× (C, D)
Figure 8:
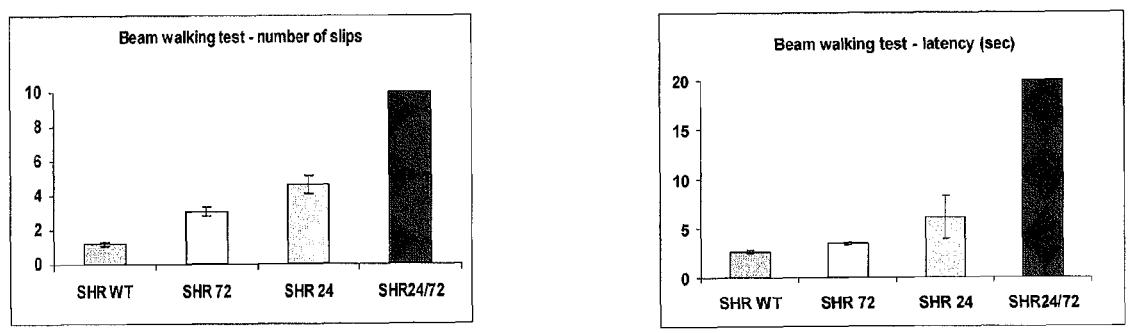
FIG. 8 Detection of neurofibrillary tangles by monoclonal antibody PHF-1 in central nervous system of the transgenic animal. PHF-1 is specific marker for tau phosphorylation. Immunoreactivity with this antibody shows that expression of Alzheimer's tau involves endogenous tau in the process of formation of NFTs. Furthermore, immunofluorescent staining shows small rod like structures similar to those observed in pre-clinical Alzheimer's disease brain tissues. Magnification: 100× (A), 200× (B), 1000× (C, D)

PAGE and Western blot. Proteins were separated on 12% denaturing polyacrylamid gel with 0.1% (w/V) SDS. Electrophoresis was performed in Tris-glycin buffer (25 mM Tris, 192 mM glycin, 0.1% SDS). Protein separation was followed by semi-dry blotting. Tris-glycin-isopropanol buffer system (25 mM Tris, 192 mM glycin, 20% Isopropanol) was used. Tau proteins were stained with antitau monoclonal antibodies DC25 which recognize tau proteins equally as a mAb 7.51 (29) and also with mAb Tau-1 (21). The positive signal was determined using anti-mouse HRP antibody and ECL method. Efficiency of blotting procedure was controled by Ponceau staining. Protein analysis has revealed the specific expression of Alzheimer's tau protein in total protein extract of brain of transgenic rat (FIG. 4) and also an expression of Alzheimer's tau protein in different brain regions of transgenic rat (FIG. 5).

Example 5

Immunohistochemical Analysis of Brain of Transgenic Rat

In order to perform immunohistochemical analysis of transgenic rat, several tau protein and Alzheimer specific monoclonal antibodies were used. Short description of monoclonal antibodies employed in these studies include PHF 1, which recognizes phosphorylated epitope Ser 396-Ser 404; mAb DC 25 recognizes phosphate independent epitope Lys347-Ile 353; mAb AT 8 recognizes phosphorylated epitope Ser 198-Ser 202; mAb Tau 1 recognizes non-phosphorylated epitope, mAb Tau 5 recognizes phosphate independent epitope. (15, 16, 17, 18, 19, 20, 21, 22)

Light Microscopy and Immunofluorescence:

Tissues were prepared and sectioned as follows. Transgenic and control animals were anaesthetized with ether and immediately perfused intracardially with buffered 4% paraformaldehyde, brains were removed, cryoprotected with 20% sucrose, quickly frozen and sectioned by cryostat at 50 µm thickness. Some of the sections were shortly pretreated with 70% formic acid prior staining procedure. Rat brain tissue sections were incubated with 1% $H_2O_2$ in PBS and non-specific binding sites were blocked with incubation in blocking medium (PBS, 0, 1% Triton, 5% normal horse serum). The immunostaining was performed using antibodies listed above, then incubated with biotinylated horse anti-mouse antibody, followed by avidin-biotin complex and visualized with VIP and DAB solution. Tissue sections were mounted on gelatin-coated slides, dried, treated with graded alcohols, xylene and coverslipped with Entellan.

Silver Staining:

Gallyas silver staining method that has been described previously (23) was adapted for free floating 50 µm sections, with gold toning.

Immunofluorescent Staining:

For indirect immunofluorescent labeling, sections were pretreated with 1% $NaHBO_4$ for 30 min. to reduce brain tissue autofluorescence. Then stained with primary antibodies at 4° C. overnight, incubated with a horse anti mouse biotinylated antibody, followed by streptavidin-Alexa 488 conjugate.

Comparison of NF pathology as seen in the brains of patients suffering from AD with those observed in the brain of transgenic animal of present invention is represented in FIG. 10.

Example 6

Figure 9:
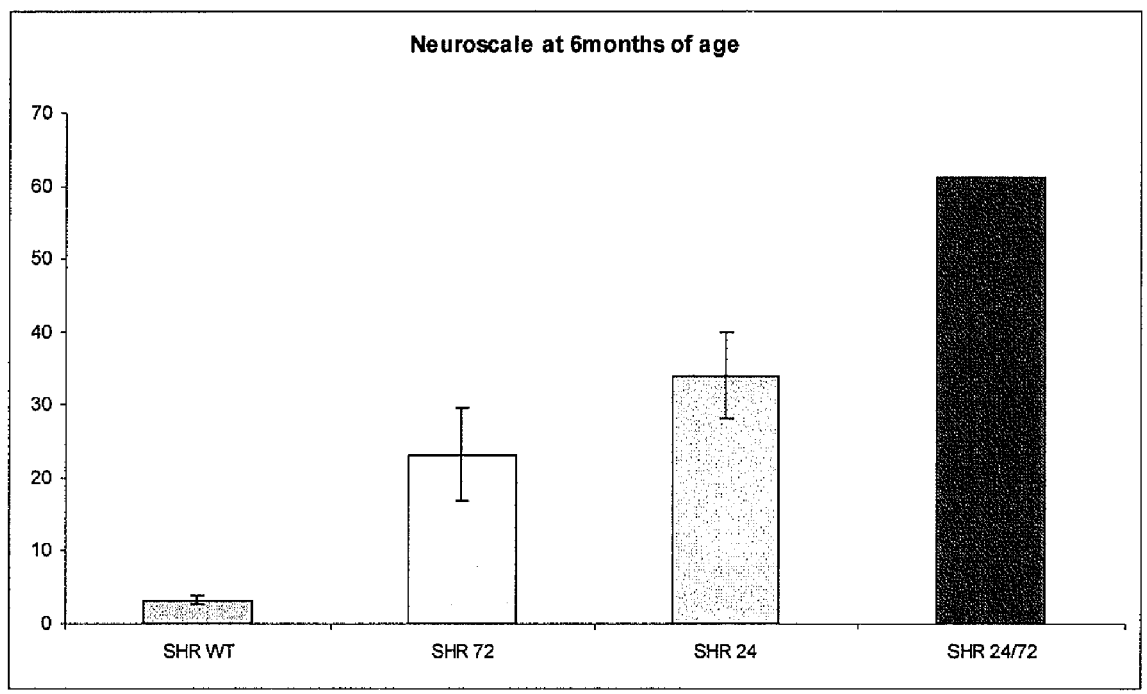
FIG. 9 Neuronal cell culture as a screening assay system for characterization of therapeutic leads and drug candidates.

A Screening Assay Systems and for Drug Leads and Drug Candidates for the Treatment and Prevention of Alzheimer's Disease The transgenic animals of the present invention can be used as a source of cells for cell culture. Both animals and cells can be used in assays of this invention. For example, cells of brain tissues expressing truncated tau gene can be cultured using standard culture techniques. The animals and cultured cells can be used as in vivo and in vitro systems for the study of the role of drug candidates on cell architecture, cell division and apoptosis as well as a morphology of primary cultured neurons, sprouting of neurites, axon branching and axon elongation in primary cultures and also for investigation of organele movement (FIG. 9). They can also be employed as a test system for neurotrophic effects of tested substances.

A study can be designed to screen for a quantitative or qualitative changes in an interaction of tau and tubulin and also in an interaction with organelle trafficking that can be modulated by tested substances.

A study can also be designed to screen for compounds that modulate the expression or activity of the cytoskeletal proteins in the process of building of synaptic connections.

A study can be also designed to screen for the compounds that can affect of NFT formation or protein-protein interaction, which could eventually lead to slowing down, inhibiting or elimination of NFT formation and this could be useful assay for screening for substances with potential of therapeutics for tauopathies and other neurodegenerative disease preferably AD. Effect of the compounds can be evaluated in cell cultures and also in vivo on the animals by means of neuropathological, neurophysiological and behavioural analysis. Many variations of screening methods are known to those of skill in the art and may be applied within the scope of the present invention.

These examples describe particular aspects and embodiments of the invention for illustrative purposes and are not limiting on the scope of the invention as listed in the claims below.

REFERENCES

1. Martin, J. B., (1999) N. Engl. J. Med. 340, 1970-1980.
2. Wischik C M, Novak M, Edwards P C, Klug A, Tichelaar W, Crowther R A (1988a) Proc Natl Acad Sci USA 85: 4884-4888
3. Wischik C M, Novak M, Trogersen H C, Edwards P C, Runswick M J, Jake R, Walker J E, Milstein C, Roth M, Klug A (1988b) Proc Natl Acad USA 85: 4506-4510

4. Hutton M, Lendon C L, Rizzu P, Baker M, Froelich S., Houlden H, Pickering-Brown S, Chackraverty S, Isaacs A, Grover A (1998) Nature 393, 702-705
5. Spillantini N G, Murrell J R, Goedert M, Farlow M R, Klug A, Ghetti B (1998) Proc Natl Acad Sci USA 95, 7737-7741.
6. Lewis J, Dickson D W, Lin W L, Chisholm L, Corral A, Jones G, Yen S H, Sahara N,
Skipper L, Yager D, Eckman C, Hardy J, Hutton M, McGowan E. Science 2001 Aug. 24;293(5534):1487-1491
7. Goedert M, Spillantini M G.: Biochem Soc Symp 2001; 67: 59-71
8. Spittaels, K., C. Van den Haute, et al.: Am J Pathol (1999), 155 (6): 2153-65.
9. Duff, K., H. Knight, et al.: Neurobiol Dis (2000) 7 (2): 87-98.
10. Czech C, Lesort M, Tremp G, Terro F, Blanchard V, Schombert B, Carpentier N, Dreisler S, Bonici B, Takashima A, Moussaoui S, Hugon J, Pradier L.: Neuroscience (1998) November; 87 (2): 325-36
11. Echeverria V and Cuello A C.: Mol Neurobiol (2002) October-December; 26(2-3):299-316
12. Breteler, M M B.: Neurobiology of Aging 21 (2000) 153-160
13. in't Veld B. A., A. Ruitenberga, A. Hofmana, B. H. Ch. Strickera, M. M. B. Bretelera,: Neurobiology of Aging 22 (2001) 407-412
14. Sambrook et al., Molecular Cloning, A Laboratory Manual, Cold Spring Harbor Laboratory Press, 1989
15. Hogan, B. et al. Manipulating the Mouse Embryo, a Laboratory Manual. Cold Spring Harbor Laboratory, 1986
16. Bramblett G T, Goedert M, Jakes R, Merrick S E, Trojanowski J Q, Lee V M.: Neuron (1993) 10: 1089-99
17. Biernat J, Mandelkow E M, Schroter C, Lichtenberg-Kraag B, Steiner B, Berling B, Meyer H, Mercken M, Vandermeeren A, Goedert M, et al.: EMBO J (1992) April; 11(4): 1593-7
18. Braak E, Braak H, Mandelkow E M: Acta Neuropathol (Berl). (1994); 87 (6): 554-67.
19. Goedert M, Jakes R, Vanmechelen E.: Neurosci Lett (1995) April 21;189(3):167-9
20. Szendrei G I, Lee V M, Otvos L Jr.: J Neurosci Res (1993) February 1;34(2): 243-9
21. Binder L I, Frankfurter A, Rebhun L I. J: Cell Biol (1985) October;101(4):1371-8
22. LoPresti P, Szuchet S, Papasozomenos S C, Zinkowski R P, Binder L I.: Proc Natl Acad Sci USA (1995) October 24;92(22):10369-73
23. Gallyas, F.: Acta Morphol.Acad.Sci.Hung. (1971) 19, 1-8.
24. Goedert M, Spillantini M G, Jakes R, Rutherford D, Crowther R A (1989) Neuron 4, 519.
25. Gordon J W, Chesa P G, Nishimura H, Rettig W J, Maccari J E, Endo T, Seravalli E, Seki T, Silver J.: Cell.1987 Jul. 31; 50 (3):445-52.
26. Damiano P F, Roson M I, Armando I, Nowicki S, Dascal E, Cuniberti L, Albornoz L E, de la Riva I J. Potential role of glycerol leading to rat fructose hypertension. Hypertension 1999 October; 34 (4Pt 2):1007-11.
27. Jackson B, Fabris B, Paxton D, Franze L, Johnston C I. High salt diet ameliorates effects of angiotension converting enzyme inhibition in spontaneously hypertensive streptozotocin diabetic rats. Clin Exp Pharmacol Physiol. 1990 March; 17(3); 229-34.
28. Turley S D, Hansen C T. Rates of sterol synthesis in the liver and extrahepatic tissues of the SHR/N-corpulent rat, an animal with hyperlipidemia and insulin-independent diabetes. J Lipid Res. 1986 May; 27(5): 486-96.
29. Novak M, Jakes R, Edwards P C, Milstein C, Wischik C M.: Proc Natl Acad Sci USA. 1991 Jul. 1; 88(13): 5837-41.

The invention claimed is:

1. A transgenic rat having germ and somatic cells whose genome comprises a transgene comprising a DNA construct comprising:

(i) a cDNA molecule coding for a transgenic truncated tau protein, wherein:

the cDNA molecule is truncated relative to a cDNA encoding full-length 4-repeat or 3-repeat human tau protein both at a 5'- or N-terminal truncation site and at a 3'- or C-terminal truncation site; wherein the 5'- or N-terminal truncation site is located at least 30 nucleotides downstream of the start codon and the 3'- or C-terminal truncation site is located at least 30 nucleotides upstream of the stop codon of the full-length human tau cDNA sequence coding for either a 4-repeat or a 3-repeat tau protein; and the cDNA molecule comprises SEQ ID No. 9; and (ii) a promoter, wherein the cDNA molecule is operably linked to the promoter, and wherein the promoter is a Thy-1 promoter; and wherein the transgenic truncated tau protein so encoded is truncated at both the N-terminus and at the C-terminus, relative to full-length human tau protein, and is expressed in the brain of the transgenic rat; and wherein neurofibrillary (NF) pathology associated with Alzheimer's disease occurs in the resulting transgenic rat expressing the transgenic truncated tau protein in the brain, when compared to non-transgenic rat counterparts.

2. A transgenic rat having germ and somatic cells whose genome comprises a transgene comprising a DNA construct comprising:
(i) a cDNA molecule coding for a transgenic truncated tau protein, wherein:
the cDNA molecule is truncated relative to a cDNA encoding full-length 4-repeat or 3-repeat human tau protein both at a 5'- or N-terminal truncation site and at a 3'- or C-terminal truncation site, wherein the 5'- or N-terminal truncation site is located at least 30 nucleotides downstream of the start codon and the 3'- or C-terminal truncation site is located at least 30 nucleotides upstream of the stop codon of the full length human tau cDNA sequence coding for either a 4-repeat or a 3-repeat tau protein; and
the cDNA molecule comprises SEQ ID No. 9; and
(ii) a tissue-specific promoter, wherein the cDNA molecule is operably linked to the tissue-specific promoter, wherein the tissue-specific promoter is functional in rat brain cells; and
wherein the transgenic truncated tau protein so encoded is truncated at both the N-terminus and at the C-terminus, relative to full-length human tau, and is expressed in the brain of the transgenic rat; and wherein
neurofibrillary (NF) pathology associated with Alzheimer's disease occurs in the resulting transgenic rat expressing the transgenic truncated tau protein in the brain when compared to non-transgenic rat counterparts.

3. A transgenic rat having germ and somatic cells whose genome comprises a transgene comprising a DNA construct comprising:
(i) a cDNA molecule coding for the transgenic truncated tau protein encoded by SEQ ID No. 3, wherein the cDNA molecule comprises SEQ ID NO. 9; and
(ii) a promoter, wherein the cDNA molecule is operably linked to the promoter, and wherein the promoter is a Thy-1 promoter; and
wherein the transgenic truncated tau protein so encoded is truncated at both the N-terminus and at the C-terminus, relative to full-length human tau protein, and is expressed in the brain of the transgenic rat; and
wherein neurofibrillary (NF) pathology associated with Alzheimer's disease occurs in the resulting transgenic rat expressing the transgenic truncated tau protein in the brain, when compared to non-transgenic rat counterparts.

4. A transgenic rat having germ and somatic cells whose genome comprises a transgene comprising a DNA construct comprising:
(i) a cDNA molecule coding for the transgenic truncated tau protein encoded by SEQ ID No. 3, wherein the cDNA molecule comprises SEQ ID NO. 9; and
(ii) a tissue-specific promoter, wherein the cDNA molecule is operably linked to the tissue-specific promoter, wherein the tissue-specific promoter is functional in rat brain cells; and
wherein the transgenic truncated tau protein so encoded is truncated at both the N-terminus and at the C-terminus, relative to full-length human tau protein, and is expressed in the brain of the transgenic rat; and
wherein neurofibrillary (NF) pathology associated with Alzheimer's disease occurs in the resulting transgenic rat expressing the transgenic truncated tau protein in the brain, when compared to non-transgenic rat counterparts.

5. A transgenic rat having germ and somatic cells whose genome comprises a transgene comprising a DNA construct comprising:
(i) a cDNA molecule coding for the transgenic truncated tau protein encoded by SEQ ID No. 12, wherein the cDNA molecule comprises SEQ ID NO. 9; and
(ii) a promoter, wherein the cDNA molecule is operably linked to the promoter, and wherein the promoter is a Thy-1 promoter; and
wherein the transgenic truncated tau protein so encoded is truncated at both the N-terminus and at the C-terminus, relative to full-length human tau protein, and is expressed in the brain of the transgenic rat; and
wherein neurofibrillary (NF) pathology associated with Alzheimer's disease occurs in the resulting transgenic rat expressing the transgenic truncated tau protein in the brain, when compared to non-transgenic rat counterparts.

6. A transgenic rat having germ and somatic cells whose genome comprises a transgene comprising a DNA construct comprising:
(i) a cDNA molecule coding for the transgenic truncated tau protein encoded by SEQ ID No. 12, wherein the cDNA molecule comprises SEQ ID NO. 9; and
(ii) a tissue-specific promoter, wherein the cDNA molecule is operably linked to the tissue-specific promoter, wherein the tissue-specific promoter is functional in rat brain cells; and
wherein the transgenic truncated tau protein so encoded is truncated at both the N-terminus and at the C-terminus, relative to full-length human tau protein, and is expressed in the brain of the transgenic rat; and
wherein neurofibrillary (NF) pathology associated with Alzheimer's disease occurs in the resulting transgenic rat expressing the transgenic truncated tau protein in the brain, when compared to non-transgenic rat counterparts.

* * * * *

UNITED STATES PATENT AND TRADEMARK OFFICE
CERTIFICATE OF CORRECTION

| | |
|---|---|
| PATENT NO. | : 8,288,608 B2 |
| APPLICATION NO. | : 10/521049 |
| DATED | : October 16, 2012 |
| INVENTOR(S) | : Eva Kontseková et al. |

Page 1 of 1

It is certified that error appears in the above-identified patent and that said Letters Patent is hereby corrected as shown below:

Title page item (75), line 1, "Eva Kontsekovà" should read --Eva Kontseková--.

Claim 2, col. 35, lines 26-27, "30nucleotides" should read --30 nucleotides--.

Signed and Sealed this
Twenty-ninth Day of January, 2013

David J. Kappos
*Director of the United States Patent and Trademark Office*